(12) United States Patent
Yale et al.

(10) Patent No.: US 7,718,096 B2
(45) Date of Patent: May 18, 2010

(54) STABILIZED ELECTROCHROMIC MEDIA

(75) Inventors: David Yale, Bethel, CT (US); Nancy Cliff, Ringwood, NJ (US); Mouhcine Kanouni, New York, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 375 days.

(21) Appl. No.: 11/475,699

(22) Filed: Jun. 27, 2006

(65) Prior Publication Data

US 2007/0002423 A1 Jan. 4, 2007

Related U.S. Application Data

(60) Provisional application No. 60/695,356, filed on Jun. 30, 2005.

(51) Int. Cl.
*C09K 9/00* (2006.01)

(52) U.S. Cl. ............... 252/583; 252/586; 106/31.43; 359/241; 359/245

(58) Field of Classification Search ............ 252/500, 252/583, 586; 359/265, 275, 241, 245; 525/391; 544/209, 198; 546/207, 14; 524/110, 94, 524/100; 526/256, 258; 106/31.43
See application file for complete search history.

(56) References Cited

U.S. PATENT DOCUMENTS

| | | | | |
|---|---|---|---|---|
| 4,590,231 A * | 5/1986 | Seltzer et al. | ............... | 524/100 |
| 4,691,015 A * | 9/1987 | Behrens et al. | ............... | 544/198 |
| 4,772,103 A | 9/1988 | Saxe | ............... | 350/362 |
| 4,902,108 A | 2/1990 | Byker | ............... | 359/265 |
| 5,096,950 A * | 3/1992 | Galbo et al. | ............... | 524/99 |
| 5,204,473 A | 4/1993 | Winter et al. | ............... | 546/188 |
| 5,239,406 A | 8/1993 | Lynam | ............... | 359/275 |
| 5,467,217 A | 11/1995 | Check, III et al. | ............... | 359/296 |
| 5,770,114 A | 6/1998 | Byker et al. | ............... | 252/583 |
| 6,045,724 A | 4/2000 | Varaprasad et al. | ............... | 252/583 |
| 6,143,209 A * | 11/2000 | Lynam | ............... | 252/583 |
| 6,178,034 B1 * | 1/2001 | Allemand et al. | ............... | 359/265 |
| 6,207,083 B1 | 3/2001 | Varaprasad et al. | ............... | 252/583 |
| 6,271,377 B1 * | 8/2001 | Galbo et al. | ............... | 546/14 |
| 6,327,069 B1 | 12/2001 | Allemand et al. | ............... | 359/265 |
| 6,403,741 B1 * | 6/2002 | Heuer et al. | ............... | 526/256 |
| 6,404,532 B1 | 6/2002 | Berneth et al. | ............... | 359/265 |
| 6,433,115 B2 * | 8/2002 | Hawker et al. | ............... | 526/258 |
| 6,441,166 B1 * | 8/2002 | Lazzari et al. | ............... | 544/209 |
| 6,545,793 B2 | 4/2003 | Berneth et al. | ............... | 359/265 |
| 6,599,326 B1 | 7/2003 | Seltzer et al. | ............... | 8/101 |
| 6,614,578 B2 | 9/2003 | Giri et al. | ............... | 359/265 |
| 6,753,844 B2 | 6/2004 | Machinda et al. | ............... | 345/107 |
| 6,753,999 B2 | 6/2004 | Zehner et al. | ............... | 359/296 |
| 6,872,832 B2 * | 3/2005 | Galbo et al. | ............... | 546/207 |
| 7,025,814 B2 * | 4/2006 | Biry | ............... | 106/31.43 |
| 7,084,196 B2 * | 8/2006 | Troutman et al. | ............... | 524/94 |
| 7,368,489 B2 * | 5/2008 | Ratzsch et al. | ............... | 524/94 |
| 7,375,149 B2 * | 5/2008 | Rotzinger et al. | ............... | 524/110 |
| 7,384,464 B2 * | 6/2008 | Wood et al. | ............... | 106/31.43 |
| 7,595,011 B2 * | 9/2009 | Kanouni et al. | ............... | 252/583 |
| 2002/0002249 A1 * | 1/2002 | Fukuda | ............... | 525/391 |
| 2002/0141032 A1 | 10/2002 | Guarr et al. | ............... | 359/265 |
| 2006/0007519 A1 * | 1/2006 | Kanouni et al. | ............... | 359/265 |

FOREIGN PATENT DOCUMENTS

JP 2002-332452 * 11/2002
WO 03/103622 12/2003

OTHER PUBLICATIONS

Patent Abstracts of Japan, vol. 17, No. 309 (Jun. 14, 1993) of JP 05 025472.
US 5,148,305, 09/1992, Byker (withdrawn)

* cited by examiner

*Primary Examiner*—Mark Kopec
*Assistant Examiner*—Khanh Tuan Nguyen
(74) *Attorney, Agent, or Firm*—Shiela A. Loggins; Joseph Suhadolnik

(57) ABSTRACT

Disclosed are compositions, which are stabilized against degradation and yellowing during exposure to ultraviolet light by the presence of certain nitroxyl, hydroxyl amine and hydroxyl amine salt additives, a method of stabilizing the compositions by the addition of said additives, to the use of such compositions as media in electroactive devices such as electrochromic and electrophoteric devices, and the electroactive devices comprised of these media.

20 Claims, No Drawings

STABILIZED ELECTROCHROMIC MEDIA

This application claims benefit under 35 USC 119(e) of U.S. provisional application No. 60/695,356, filed Jun. 30, 2005.

The present invention relates to compositions which are stabilized against degradation and yellowing during exposure to ultraviolet light, to the method of stabilizing the compositions, to the use of such compositions as media in electroactive devices such as electrochromic and electrophoretic devices, and the electroactive devices comprised of these media.

BACKGROUND OF THE INVENTION

A major problem which limits the usefulness and useful lifetime of materials exposed to ultraviolet (UV) radiation is degradation associated with such exposure. This degradation results from decomposition and other chemical reactions of the materials initiated by absorption of ultraviolet light. Among the undesired consequences of these chemical reactions can be discoloration of the material. Among the materials that are particularly affected by UV induced discoloration are solvents that comprise the media of functional devices such as electroactive devices, including electrochromic and electrophoretic devices.

Copending U.S. patent application Ser. No. 11/171,176 filed Jun. 30, 2005, incorporated herein in its entirety by reference, discloses media useful in electroactive stabilized with UV absorbers and certain N—H, N—OR and N-Alkyl hindered amine light stabilizers (HALS).

Electrochromic devices are well known, e.g., U.S. Pat. Nos. 4,902,108 and 6,178,034. Such devices undergo a change in electromagnetic radiation transmission upon application of an electrical stimulus and have found use in a number of commercial applications. For example, they may be employed in glazings, e.g., energy efficient and privacy windows for architectural or automotive use, automotive rearview mirrors, displays, filters, eyewear, antidazzle and fog penetrating devices, and other applications where variable light transmission is desired. In many of these applications the device is routinely exposed to harmful environmental conditions, including exposure to UV light as from the sun.

Electrochromic devices are typically associated with a noticible change in color. Changes in other optical properties, such as in the degree of clarity and opacity and absorption in the IR, are also characteristics of such devices. The compositions of the present invention can also be employed as part of other electroactive devices associated with similar activity such as liquid crystal and suspended particle devices, including, as examples, electronic paper and privacy windows.

U.S. Pat. Nos. 6,614,578; 5,770,114; 6,207,083 and 6,045,724, which are incorporated herein in their entirety by reference, disclose solvent containing media for electrochromic devices which protect the device by absorbing UV light either through an intrisic property of the solvent or by the addition of UV absorbing additives (UVAs), e.g., benzotriazoles, benzophenones, cyanoacrylates and others.

U.S. Pat. No. 5,148,305 claims compositions with certain cyanoacrylate UVAs in specified electrochromic solutions due to the greater solubility than similar solutions containing certain benzotriazoles, benzophenones, and/or oxanilides.

U.S. Pat. Nos. 6,614,578 and 5,770,114 disclose media for electrochromic devices containing benzotriazole UVAs that are substituted with groups to provide improved solubility.

U.S. Pat. No. 5,239,406, which is incorporated herein in its entirety by reference, discloses a multi-layered electrochromic glazing assembly, at least one layer of which comprises an additive for absorbing, blocking, and/or screening ultraviolet radiation. Said additive may be in one of the polymeric layers of the invention or in the electrochromic medium itself.

U.S. Pat. Nos. 6,143,209; 6,327,069; 6,404,532 and 6,545,793, which are incorporated herein in their entirety by reference, describe electrochromic devices comprising a solvent and optionally UV absorbers including benzophenones, cyanoacrylates, salicylates and benzotriazoles.

Even with the addition of UV absorbing additives, discoloration of the media upon exposure to UV light remains a problem. In addition to UVA's, other stabilizing additives, including hindered amine light stabilizers (HALS), have been used in electrochromic media, for example, U.S. Pat. Nos. 6,178,034 and 5,239,406, and U.S. Pat Appl Pub. 2002/0141032.

Electrophoretic devices are also well known, particularly those comprised of suspended particles, e.g., U.S. Pat. Nos. 4,772,103; 6,753,844 and 6,753,999 which are incorporated herein in their entirety by reference. They can be commercially employed in many of the same applications as electrochromic devices, e.g., glazings and displays and are subject to similar photodegradation. U.S. Pat. No. 5,467,217, incorporated herein in its entirety by reference, discloses electrophoretic light valve compositions stabilized with UV light absorbers.

U.S. Pat. No. 6,599,326, which is incorporated herein in its entirety by reference, teaches the stabilization of pulp or paper with dialkylhydroxylamines or substituted dialkylhydroxylamines or their salts.

U.S. patent application Ser. No. 10/512,528 filed Apr. 24, 2003 and Ser. No. 10/970,112 filed Oct. 21, 2004, which are incorporated herein in their entirety by reference, teach stabilization of body care products, household products, textiles and fabrics with hindered nitroxyls, sterically hindered hydroxylamines and hydroxylamine salts and with dialkylhydroxylamines or substituted dialkylhydroxylamines or their salts.

It has been found that certain nitrones, hydroxylamines and hydroxylamine salts are effective preventing the yellowing of solutions containing UVAs found in electroactive devices.

DESCRIPTION OF THE INVENTION

The present invention relates to compositions which are suitable as a medium in electroactive devices which comprise
  i) one or more solvents suitable as a medium in an electroactive device,
  ii) an effective amount of one or more additive compounds selected from the group consisting of the ultraviolet light absorbers and
  iii) an effective amount of one or more additive compounds selected from the group consisting of nitroxyls, hydroxylamines and hydroxylamine salts of the following formulae:

-continued

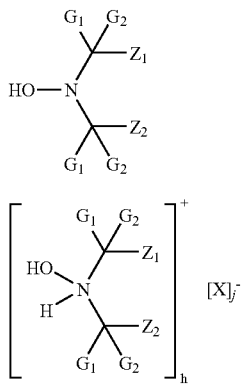

(II)

(III)

$R_1R_2N—OH$ (IV)

$(R_1R_2N—OH).(HY)$ (V).

The present invention also pertains to a method of preparing a stabilized medium useful in electroactive devices, which method comprises the addition of an effective amount of one or more additive compounds selected from the group consisting of nitroxyls, hydroxylamines and hydroxylamine salts to a composition comprising i) one or more solvents solvent suitable as a medium in an electroactive device and ii) an effective amount of one or more additive compounds selected from the group consisting of the ultraviolet light absorbers.

The present invention also pertains to electroactive devices, such as electrochromic and electrophoretic devices, which comprise the stabilized compositions of the present invention.

In the present discussion, the following definitions apply:

"Anodic Material"—is meant to refer to a compound or composition capable of undergoing a reversible color change when its valence state is altered due to oxidation.

"Cathodic Material"—is meant to refer to a compound or composition capable of undergoing reversible color change when its valence state is altered due to reduction.

"Electroactive"—is meant to refer to either a compound, mixture of compounds, solution, composition or device capable of undergoing a reversible change of composition or property, for example, color, oxidation state, conductivity, opacity, optical clarity, diffractive index, electromagnetic transmittance, modulus, adhesion, pH, permeability among others when subjected to electrical stimulus." Examples of electroactive devices include electrochromic and electrophoretic devices.

"Electrochromic"—is meant to refer to either a compound, mixture of compounds, solution, composition or device capable of undergoing a reversible change in electromagnetic absorption/transmittance when subjected to electrical stimulus.

"Electrophoretic"—is meant to refer to either a compound, mixture of compounds, particle, suspension, solution, composition or device capable of undergoing a reversible change in the geometric orientation of at least one component when subjected to electrical stimulus. Suspended particle devices are the most pertinent to the present invention as in, for example, the electrophoretic display in U.S. Pat. Appl. 2003/0020844 which is incorporated herein in its entirety by reference.

"Yellowing"—is meant to refer to increase in color of the solution over time. Typically the color formed is in fact yellow, but given the nature of organic degradation reactions, the color formed may also be various shades of yellow and other hues including brown.

Electrochromic devices require a pair of electrodes and at least one compound or material that changes transmittance upon or after application of an electric stimulus.

The electrochromic devices of the present invention typically comprise: (a) a first substantially transparent substrate having an electrically conductive material associated therewith; (b) a second substrate having an electrically conductive material associated therewith; and (c) an electrochromic medium which comprises: (1) at least one solvent; (2) at least one anodic material; (3) at least one cathodic material, wherein either or both of the anodic and cathodic materials are electroactive and at least one of the anodic and cathodic materials is electrochromic; and (4) may also comprise a non-electrochromic, current carrying electrolyte.

Examples can be found in:

U.S. Pat. No. 4,902,108, which is incorporated herein in its entirety by reference, describes single-compartment, self-erasing, solution-phase electrochromic device.

U.S. Pat. No. 6,178,034, which is incorporated herein in its entirety by reference, describes a multi-layered electrochromic device useful for large area glazings.

U.S. Pat. Appl. 2002/0241032, which is incorporated herein in its entirety by reference, describes electrochromic media and devices.

U.S. Pat. Nos. 6,143,209; 6,327,069; 6,404,532 and 6,545,793, which are incorporated herein in their entirety by reference, describe electrochromic devices comprising a solvent and UV absorbing additives.

The anodic and cathodic materials may also be combined or linked by a bridging unit as described in U.S. Pat. No. 6,241,916 which is hereby incorporated herein by reference in its entirety. It is also possible to link anodic materials or cathodic materials by similar methods. The concepts described can further be combined to yield a variety of electroactive materials that are linked or coupled, including linking of a redox buffer such as linking of a color-stabilizing moiety to an anodic and/or cathodic material. The anodic and cathodic electrochromic materials can also include coupled materials as described in U.S. Pat. No. 6,249,369 which is hereby incorporated herein by reference in its entirety.

The electrochromic devices can additionally include near infrared (NIR) absorbing compounds as described in U.S. Pat. No. 6,193,912 which is also hereby incorporated herein by reference in its entirety. In addition, electrochromic medium may comprise other materials, such as thermal stabilizers, antioxidants, thickeners, viscosity modifiers, tint providing agents, redox buffers, and mixtures thereof.

Additionally, a single-layer, single-phase medium may include a medium where the anodic and cathodic materials are incorporated into a polymer matrix as is described in U.S. Pat. No. 6,569,361 which is incorporated herein in its entirety by reference. The anodic or cathodic materials may also comprise a conductive polymer with inherent electrochromic activity.

Multi-layer devices are known. The medium may be made up in layers and includes a material attached directly to an electrically conducting electrode or confined in close proximity thereto which remains attached or confined when electrochemically oxidized or reduced.

Multi-phase media are also known. One or more materials in the medium undergoes a change in phase during the operation of the device, for example a material contained in solution in the ionically conducting electrolyte forms a layer on the electrically conducting electrode when electrochemically oxidized or reduced.

For purposes of the present disclosure, the solvent containing component of the electrochromic device need not contain any of the functional elements, electroactive or otherwise, of the electrochromic device. In practice, however, one would expect that as the solvent is useful as media for the electrochromic materials it would contain some functional aspect of the device be it an electrolyte, anodic material(s), cathodic material(s), or any combination thereof, and may comprise other components as well, as understood in the electrochromic device art.

The anodic active, cathodic active, and electrolyte materials, as well as the other materials of the electrochromic devices, and the concentrations used, can be found in the patents cited herein.

Among the solvents suitable for the invention are those known in the art of solution-phase electrochromic devices to be suitable for the dissolution of one or more of an anodic electrochromic compound, a cathodic electrochromic compound, and/or a material functioning as a charge carrying electrolyte in order to provide an electroactive medium of an electrochromic device. For example, at least one of the one or more solvents is selected from the group consisting of sulfones, amides, sulfoxides, ethers, polyethers, alcohols, polyols, nitriles, ketones, aldehydes, carboxylic acids, cyclic esters, cyclic carbonates, glycidyl ether carbonates and silicon/polyol co-polymers.

For example, at least one of the one or more solvents is selected from the group consisting of sulfones, ketones, nitriles and cyclic carbonates.

Such solvents include, among others, commercially available 3-methylsulfolane, tetramethylene sulfone, N,N-dimethylformamide, dimethyl sulfoxide, tetraglyme and other polyethers, alcohols such as methanol, ethanol, ethoxyethanol, nitriles, such as acetonitrile, glutaronitrile, 3-hydroxypropionitrile, methoxypropionitrile, 3-ethoxypropionitrile 2-methylglutaronitrile, cyanoethyl sucrose, ketones including acetone, methyl ethyl ketone, cyclopentanone, cyclohexanone, benzoyl acetone, 4-hydroxy-4-methyl-2-pentanone, acetophenone, carboxylic acids such as acetic acid, cyclic esters including beta-propiolactone, 2-acetylbutyrolactone, gamma-butyrolactone, gamma-valerolactone, 4-ethenyl-1,3-dioxalane-2-one, propylene carbonate (PC), ethylene carbonate, 1,2-butylene carbonate, glycidyl ether carbonates (such as those commercially available from Texaco Chemical Company, Austin, Tex.) silicon/polyol co-polymers, (such as those available from Genesse Polymers, Flint, Mich.), and combinations thereof and homogenous mixtures of the same.

For example, at least one of the one or more solvents is selected from the group consisting of 3-methylsulfolane, tetramethylene sulfone, N,N-dimethylformamide, dimethyl sulfoxide, tetraglyme or other polyether, methanol, ethanol, ethoxyethanol, acetonitrile, glutaronitrile, 3-hydroxypropionitrile, methoxypropionitrile, 3-ethoxypropionitrile 2-methylglutaronitrile, cyanoethyl sucrose, acetone, methyl ethyl ketone, methyl amyl ketone, cyclopentanone, cyclohexanone, benzoyl acetone, 4-hydroxy-4-methyl-2-pentanone, acetophenone, acetic acid, beta-propiolactone, 2-acetylbutyrolactone, gamma-butyrolactone, gamma-valerolactone, 4-ethenyl-1,3-dioxalane-2-one, propylene carbonate, ethylene carbonate and 1,2-butylene carbonate.

For example, at least one of the one or more solvents is selected from the group consisting of 3-methylsulfolane, tetramethylene sulfone, tetraglyme, acetone, methyl ethyl ketone, methyl amyl ketone, cyclopentanone, cyclohexanone, acetonitrile, glutaronitrile, 3-hydroxypropionitrile, methoxypropionitrile, 3-ethoxypropionitrile 2-methylglutaronitrile, 4-ethenyl-1,3-dioxalane-2-one, propylene carbonate, ethylene carbonate and 1,2-butylene carbonate.

For example, at least one of the one or more solvents is selected from the group consisting of tetraglyme, methyl amyl ketone, acetonitrile and propylene carbonate.

More than one solvent may be used.

The media comprising the solvent may also be dispersed within a polymer or co-polymer matrix as described in, for example, U.S. Pat. No. 5,928,572 which is incorporated herein in its entirety by reference. This interspersed layer may exist as a free standing gel.

Monomers with the appropriate polymerization initiators can be used as a monomer composition so that this composition can be in-situ polymerized after the cell has been filled by radiation, heat, or electrogenerated initiators to form a solid. Such processes are described, for example, in U.S. Pat. No. 6,020,987 which is incorporated herein in its entirety by reference.

U.S. Pat. No. 6,020,987, describes an improved electrochromic medium comprising at least three electroactive materials having absorption spectra when activated that add together such that the color of the electrochromic medium can be pre-selected by individually choosing the concentrations of the at least three electroactive materials.

For purposes of the present disclosure, the solvent composition need not contain any of the functional elements, electroactive or otherwise, of the electrochromic device, except for the UV stabilizers. In practice, however, one would expect the solvent to be used as a media for some functional aspect of the device be it an electrolyte, anodic material(s), cathodic material(s), or any combination thereof and may comprise other components common in the electrochromic device art, e.g., tinting materials, heat stabilizers, infrared absorbing dyes, moisture scavengers, fillers, viscosity modifiers, etc. If an opaque layer is desired, such as in display applications, then the solution may contain at least one additive selected from the group consisting of inert inorganic oxide fillers, inorganic sulfate fillers, inorganic carbonate fillers, inorganic pigments, organic pigments, surfactants, plasticizers and dispersing agents.

The composition of the present invention is also useful as the suspending fluid in electrophoretic devices, examples of which can be found in U.S. Pat. Nos. 4,247,175; 4,407,565; 4,772,103; 6,753,844 and 6,753,999 and U.S. Pat. Appl. 2003/002084 incorporated herein in their entirety by reference.

Solvents useful in electrophoretic devices include organic solvents, such as halogenated organic solvents, saturated linear or branched hydrocarbons, silicone oils, and low molecular weight halogen-containing polymers are some useful suspending fluids.

Useful organic solvents include, but are not limited to, epoxides, such as, for example, decane epoxide and dodecane epoxide; vinyl ethers, such as, for example, cyclohexyl vinyl ether; aromatic hydrocarbons, such as, for example, toluene and naphthalene. Halogenated organic solvents include, but are not limited to, tetrafluorodibromoethylene, tetrachloroethylene, trifluorochloroethylene, 1,2,4-trichlorobenzene and carbon tetrachloride. Hydrocarbons include, but are not limited to, dodecane, tetradecane, normal paraffinic liquids, naphtha, and other petroleum solvents. Silicone oils include, but are not limited to, octamethyl cyclosiloxane and higher molecular weight cyclic siloxanes, poly(methyl phenyl siloxane), hexamethyldisiloxane, and polydimethylsiloxane. Low molecular weight halogen-containing polymers include, but are not limited to, poly(chlorotrifluoroethylene) polymers and perfluorinated ethers.

Alcohols include methanol and 2-ethylhexanol. Esters include alkyl acetates including isopentyl acetate, alkylphenyl acetates including p-nonylphenyl acetate, diesters including dioctylphthalate, diisodecyl adipate, dioctyl sebacate and hindered esters including 3,5,5-trimethylhexyl isobutyrate, 3,5,5-trimethylhexyl neopentanoate, neopentyl neopentanoate and isobutyl neopentanoate. Useful ethers include di-2-ethylhexyl ether, di-3,5,5-trimethylhexyl ether, di-neopentyl ether and non-symmetrical branched ethers.

The electrophoretic suspending fluid may comprise one or more solvents. Other materials common in the art may also be present, such as surfactants, water, polymers, surface modifiers, charge control agents and charge adjuvants. Reactants or solvents for the microencapsulation process (oil soluble monomers, for example) can also be contained in the suspending fluid.

While the liquid suspension can be used as such as the light-modulating element, it is also possible to create a light-modulating film by having droplets of a liquid suspension distributed in a polymer matrix, e.g., U.S. Pat. Nos. 3,257,905; 3,341,274; 4,919,521; 5,463,491 and 5,463,492 which are incorporated herein by reference.

Thus, a film suitable for use in a electrophoretic device may comprise a cross-linked polymer matrix having droplets of a electrophoretic suspension distributed in the matrix. This film may be swollen with a suitable liquid. This improves the frequency response characteristics of the resulting film and reduces light scatter.

U.S. Pat. Nos. 5,467,217 and 4,407,565, incorporated herein in their entirety by reference, describe fluid suspensions for electrophoretic devices stabilized against photodegradation by incorporation of UVAs, specifically benzotriazole and cyanoacrylate UVAs respectfully. No mention is made of other stabilizers.

The UVAs chosen for the present compositions must be of sufficient solubility in the chosen solvent to be contained at an effective level. For example, U.S. Pat. Nos. 5,148,305; 6,614,578 and 5,770,114 base their selection of specific UVA compounds based on the solubility of the UVA in the electrochromic media solvent.

The present ultraviolet light absorbers (UVAs) are selected from the group consisting of the hydroxyphenylbenzotriazoles, the benzophenones, the benzoxazones, the α-cyanoacrylates the oxanilides, the tris-aryl-s-triazines, the cinnamates, the malonates, the benzoates, terephthalic and isophthalic acids with resorcinol and phenols, benzilidenes, and the salicylates.

More than one UVA may be selected and used together.

For example, at least one of the one or more ultraviolet light absorbers is selected from the group consisting of hydroxyphenylbenzotriazoles, benzophenones, and tris-aryl-s-triazines.

The present hydroxyphenylbenzotriazole UV absorbers are disclosed for example in U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905; 4,853,471; 5,268,450; 5,278,314; 5,280,124; 5,319,091; 5,410,071; 5,436,349; 5,516,914; 5,554,760; 5,563,242; 5,574,166; 5,607,987; 5,770,114; 5,977,219; 6,166,218; 6,262,151; 6,392,056; 6,451,887; 6,458,872 and 6,614,578 the disclosure of which are hereby incorporated by reference.

The present tris-aryl-s-triazine UV absorbers are disclosed for example in U.S. Pat. Nos. 3,843,371; 4,619,956; 4,740, 542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,736,597; 5,942,626; 5,959,008; 5,998,116; 6,013,704; 6,060,543; 6,242,598 and 6,255,483, the disclosures of which are hereby incorporated by reference.

The present benzophenone UV absorbers are for example derivatives of 2,4 dihydroxy benzophenone; 2,2',4, trihydroxy benzophenone; and 2,2',4,4,-tetrahydroxybenzophenone as found in the art and the patents cited herein.

The present cyanoacrylate, cinnamate and malonate UV absorbers are for example derivatives of α-cyano-β,β-diphenylacrylic acid; cinnamic acid; α-cyano-β-methylcinnamic acid; and benzylidenemalonates as found in the art and the patents cited herein.

For example, UV absorbers useful in the instant invention are those found in U.S. Pat. Nos. 5,148,305; 6,614,578; 5,770, 114; 6,143,209; 6,327,069; 6,545,793 and 6,404,532 which are incorporated in their entirety by reference.

For example, UV absorbers useful in the instant invention are those found in U.S. Pat. Nos. 6,614,578 and 5,770,114 which are incorporated in their entirety by reference.

For example UV absorbers useful in the instant invention are selected from the group consisting of 2-hydroxybenzophenone substituted in the 4-position by hydroxy, $C_1$-$C_{12}$ alkoxy, $C_1$-$C_{12}$ branched alkoxy or said alkoxy or branched alkoxy substituted by one or more hydroxy and/or interrupted by one or more oxygen atoms, 2-[2-hydroxy-5-($C_1$-$C_{12}$ alkyl or branched alkyl)phenyl]-2H-benzotriazole, 2-[2-hydroxy-3-($C_1$-$C_{12}$ alkyl or branched alkyl)-5-($C_1$-$C_{12}$ alkyl or branched alkyl)phenyl]-2H-benzotriazole, 2-[2-hydroxy-3,5-di(α,α-dimethylbenzyl)phenyl]-2H-benzotriazole, 2-[2-hydroxy-3-(α,α-dimethylbenzyl)-5-($C_1$-$C_{12}$ alkyl or branched alkyl)]-2H-benzotriazole, $C_1$-$C_{18}$ alkyl or branched alkyl esters of 3-(benzotriazol-2-yl)-5-tert-butyl-4-hydroxyhydro-cinnamic acid, 2-methoxyethyl 3-(benzotriazol-2-yl)-5-tert-butyl-4-hydroxyhydrocinnamate, 2-(2-methoxyethoxy)ethyl 3-(benzotriazol-2-yl)-5-tert-butyl-4-hydroxyhydrocinnamate, 2-[2-(2-methoxyethoxy)ethoxy]ethyl 3-(benzotriazol-2-yl)-5-tert-butyl-4-hydroxyhydro-cinnamate, 2-{2-hydroxy-3-tert-butyl-5-[2-(omega-hydroxy-octa(ethyleneoxy)carbonyl)ethyl]phenyl}-2H-benzotriazole, 5-chloro-2-[2-hydroxy-5-($C_1$-$C_{12}$ alkyl or branched alkyl)phenyl]-2H-benzotriazole, 5-chloro-2-[2-hydroxy-3-($C_1$-$C_{12}$ alkyl or branched alkyl)-5-($C_1$-$C_{12}$ alkyl or branched alkyl)phenyl]-2H-benzotriazole, 5-chloro-2-[2-hydroxy-3,5-di(α,α-dimethylbenzyl)phenyl]-2H-benzotriazole, 5-chloro-2-[2-hydroxy-3-(α,α-dimethylbenzyl)-5-($C_1$-$C_{12}$ alkyl or branched alkyl)]-2H-benzotriazole, $C_1$-$C_{18}$ alkyl or branched alkyl esters of 3-(5-chloro-benzotriazol-2-yl)-5-tert-butyl-4-hydroxyhydrocinnamic acid, 2-methoxyethyl 3-(5-chloro-benzotriazol-2-yl)-5-tert-butyl-4-hydroxyhydrocinnamate, 2-(2-methoxyethoxy)ethyl 3-(5-chloro-benzotriazol-2-yl)-5-tert-butyl-4-hydroxyhydro-cinnamate, 2-[2-(2-methoxyethoxy)ethoxy]ethyl 3-(5-chloro-benzotriazol-2-yl)-5-tert-butyl-4-hydroxy-hydrocinnamate, 5-chloro-2-{2-hydroxy-3-tert-butyl-5-[2-(omega-hydroxy-octa(ethyleneoxy)carbonyl)-ethyl]phenyl}-2H-benzotriazole, 5-trifluoro-2-[2-hydroxy-5-($C_1$-$C_{12}$ alkyl or branched alkyl) phenyl]-2H-benzotriazole,
5-trifluoro-2-[2-hydroxy-3-($C_1$-$C_{12}$ alkyl or branched alkyl)-5-($C_1$-$C_{12}$ alkyl or branched alkyl)phenyl]-2H-benzotriazole,
5-trifluoro-2-[2-hydroxy-3,5-di(α,α-dimethylbenzyl)phenyl]-2H-benzotriazole,
5-trifluoro-2-[2-hydroxy-3-(α,α-dimethylbenzyl)-5-($C_1$-$C_{12}$ alkyl or branched alkyl)]-2H-benzotriazole,
$C_1$-$C_{18}$ alkyl or branched alkyl esters of 3-(5-trifluoro-benzotriazol-2-yl)-5-tert-butyl-4-hydroxyhydrocinnamic acid,
2-methoxyethyl 3-(5-trifluoro-benzotriazol-2-yl)-5-tert-butyl-4-hydroxyhydrocinnamate,
2-(2-methoxyethoxy)ethyl 3-(5-trifluoro-benzotriazol-2-yl)-5-tert-butyl-4-hydroxyhydro-cinnamate,
2-[2-(2-methoxyethoxy)ethoxy]ethyl 3-(5-trifluoro-benzotriazol-2-yl)-5-tert-butyl-4-hydroxy-hydrocinnamate,
5-trifluoro-2-{2-hydroxy-3-tert-butyl-5-[2-(omega-hydroxy-octa(ethyleneoxy)carbonyl)-ethyl]phenyl}-2H-benzotriazole
$C_1$-$C_{18}$ alkyl or branched alkyl esters of p-methoxycinnamic acid,
$C_1$-$C_{18}$ alkyl or branched alkyl esters of p-methoxybenzylidenemalonic acid,
$C_1$-$C_{18}$ alkyl or branched alkyl esters of 2-cyano-3,3-diphenylacrylic acid,
di-(1,2,2,6,6-pentamethylpiperidin-4-yl) p-methoxybenzylidenemalonate,
2,4-bis(2,4-dimethylphenyl)-6-(2-hydroxy-4-($C_1$-$C_{12}$ alkyl or branched alkyl)oxyphenyl)-s-triazine,
2,4-diphenyl-6-(2-hydroxy-4-($C_1$-$C_{12}$ alkyl or branched alkyl)oxyphenyl)-s-triazine,
2,4-bis(2,4-dimethylphenyl)-6-[2-hydroxy-4-(3-do-/tri-decyloxy-2-hydroxypropoxy)phenyl]-s-triazine,
2,4-bis(2,4-dimethylphenyl)-6-[2-hydroxy-4-(3-do-/tri-decyloxy-2-hydroxypropoxy)-5-α-cumylphenyl]-s-triazine,
2-[2-hydroxy-4-(1-($C_1$-$C_{18}$ alkyl or branched alkyl)oxycarbonylethoxy)phenyl]-4,6-bis(4-phenylphenyl)-1,3,5-triazine, and
the reaction product of 2,4,6-tris(2,4-dihydroxyphenyl)-s-triazine with octyl α-haloacetate.

For example, UV absorbers useful in the instant invention are selected from the group consisting of
4-methoxy-2-hydroxybenzophenone,
4-octyloxy-2-hydroxybenzophenone,
4-dodecyloxy-2-hydroxybenzophenone,
4-(2-ethylhexyloxy)-2-hydroxybenzophenone,
2,4-dihydroxybenzophenone,
4-methoxy-2,2'-dihydroxybenzophenone,
4,4'-dimethoxy-2,2'-dihydroxybenzophenone,
2-(2-hydroxy-5-methylphenyl)-2H-benzotriazole,
2-(2-hydroxy-5-tert-octylphenyl-2H-benzotriazole,
2-(2-hydroxy-3,5-di-tert-amylphenyl)-2H-benzotriazole,
2-(2-hydroxy-3-sec-butyl-5-tert-butylphenyl)-2H-benzotriazole,
2-(2-hydroxy-3-dodecyl-5-methylphenyl)-2H-benzotriazole,
2-[2-hydroxy-3,5-di(α,α-dimethylbenzyl)phenyl]-2H-benzotriazole,
2-[2-hydroxy-3-(α,α-dimethylbenzyl)-5-tert-octylphenyl]-2H-benzotriazole,
octyl 3-(benzotriazol-2-yl)-5-tert-butyl-4-hydroxyhydrocinnamate,
butyl 3-(benzotriazol-2-yl)-5-tert-butyl-4-hydroxyhydrocinnamate,
pentyl 3-(benzotriazol-2-yl)-5-tert-butyl-4-hydroxyhydrocinnamate,
2-methoxyethyl 3-(benzotriazol-2-yl)-5-tert-butyl-4-hydroxyhydrocinnamate,
2-(2-methoxyethoxy)ethyl 3-(benzotriazol-2-yl)-5-tert-butyl-4-hydroxyhydrocinnamate,
2-[2-(2-methoxyethoxy)ethoxy]ethyl 3-(benzotriazol-2-yl)-5-tert-butyl-4-hydroxyhydro-cinnamate,
2-{2-hydroxy-3-tert-butyl-5-[2-(omega-hydroxy-octa(ethyleneoxy)carbonyl)ethyl]phenyl}-2H-benzotriazole,
5-chloro-2-(2-hydroxy-3-tert-butyl-5-methylphenyl)-2H-benzotriazole,
5-chloro-2-(2-hydroxy-3,5-di-tert-butylphenyl)-2H-benzotriazole,
octyl 3-(5-chlorobenzotriazol-2-yl)-5-tert-butyl-4-hydroxyhydrocinnamate,
octyl 3-(5-trifluoromethyl-benzotriazol-2-yl)-5-tert-butyl-4-hydroxyhydrocinnamate,
butyl 3-(5-trifluoromethyl-benzotriazol-2-yl)-5-tert-butyl-4-hydroxyhydrocinnamate,
pentyl 3-(5-trifluoromethyl-benzotriazol-2-yl)-5-tert-butyl-4-hydroxyhydrocinnamate,
5-triflouromethyl-2-{2-hydroxy-3-tert-butyl-5-[2-(omega-hydroxy-octa(ethyleneoxy)-carbonyl)ethyl]phenyl}-2H-benzotriazole,
2-(2-methoxyethoxy)ethyl 3-(5-trifluoromethylbenzotriazol-2-yl)-5-tert-butyl-4-hydroxy-hydrocinnamate,
2-[2-(2-methoxyethoxy)ethoxy]ethyl 3-(5-trifluoromethyl-benzotriazol-2-yl)-5-tert-butyl-4-hydroxyhydrocinnamate,
2,4-bis(2,4-dimethylphenyl)-6-(2-hydroxy-4-octyloxyphenyl)-s-triazine,
2,4-bis(2,4-dimethylphenyl)-6-[2-hydroxy-4-(3-do-/tri-decyloxy-2-hydroxypropoxy)phenyl]-s-triazine,
2-[2-hydroxy-4-(1-octyoxycarbonylethoxy)phenyl]-4,6-bis(4-phenylphenyl)-1,3,5-triazine and
the reaction product of 2,4,6-tris(2,4-dihydroxyphenyl)-s-triazine with octyl α-haloacetate.

Like the UVAs, the nitroxyls, hydroxylamines and hydroxylamine salts chosen for the present compositions must be of sufficient solubility in the chosen solvent to be contained at an effective level. They must also not interfere with th functioning of the device, for example, they must not hinder the color change of an electrochromic device.

More than one nitroxyl, hydroxylamine and/or hydroxylamine salt may be selected and used together.

Dialkylhydroxylamine stabilizers of formula IV, for example N,N,-dialkylhydroxylamines and N,N-dibenzylhydroxylamine, are well known as useful stabilizers for a variety of polymeric substrates as is taught for example in U.S. Pat. Nos. 4,590,231, 4,668,721, 4,782,105, 4,876,300 and 5,013,510, the relevant parts of which are incorporated herein by reference.

U.S. Pat. Nos. 4,649,221 and 4,703,073 teach the use of polyhydroxylamine compounds and alkylated N,N-dibenzylhydroxylamine derivatives, respectively, towards stabilizing polyolefins. The disclosures of these U.S. patents are also hereby incorporated by reference.

Ester, amide or thio substituted N,N-dialkylhydroxylamines are described in U.S. Pat. Nos. 4,612,393, 4,720,517 and 5,019,285, the relevant disclosures of which are also hereby incorporated by reference.

For example, the present dialkylhydroxylamine stabilizers of formula IV are those disclosed in the above mentioned U.S. patents, and are for instance of the formula

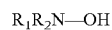

$R_1R_2N$—OH where $R_1$ is alkyl of 1 to 36 carbon atoms, cycloalkyl of 5 to 12 carbon atoms or aralkyl of 7 to 9 carbon atoms; or $R_1$ is said alkyl, cycloalkyl or aralkyl substituted by one to six alkyl of 1 to 12 carbon atoms, halogen, cyano, $E_1O—$, $E_1CO—$, $E_1OCO—$, $E_1COO—$, $E_1S—$, $E_1SO—$, $E_1SO_2—$, $—NH_2$, $—NHE_1$, $—NE_1E_2$, $—PO(OE_1)(OE_2)$ or $—OPO(OE_1)(OE_2)$ groups;

$R_2$ is hydrogen or independently has the same meaning as $R_1$, where at least one of $R_1$ and $R_2$ contains a hydrogen alpha to the —NOH moiety; or $R_1$ and $R_2$ together form a $C_{2-12}$heterocyclic ring which contains at least one carbon substituted hydrogen alpha to the —NOH moiety, where said $C_2$-$C_{12}$heterocyclic ring is unsubstituted or is substituted by one to three alkyl of 1 to 12 carbon atoms, halogen, cyano, $E_1O—$, $E_1CO—$, $E_1OCO—$, $E_1COO—$, $E_1S—$, $E_1SO_2—$, $E_1SO_2—$, $—NH_2$, $—NHE_1$, $—NE_1E_2$, $—PO(OE_1)(OE_2)$ or $—OPO(OE_1)(OE_2)$ groups; or where said $C_{2-12}$heterocyclic ring is interrupted by one to three $—O—$, $—NE_1-$, $—CO—$, $—CONE_1-$, $—S—$, $—SO—$, $—SO_2—$, $—COO—$, $—PO_3—$ or $—PO_4E_1$ groups; or where said heterocyclic ring is both substituted and interrupted by said groups; and $E_1$ and $E_2$ independently are hydrogen, alkyl of 1 to 4 carbon atoms or alkyl of 1 to 4 carbon atoms substituted by one to three hydroxyl groups; or $E_1$ and $E_2$ independently are an oligomer of poly(ethylene glycol) or poly(propylene glycol) terminated by hydroxyl, methoxy, acetate or propionate, where the oligomer has a molecular weight up to about 500.

The phrase "where at least one of $R_1$ and $R_2$ contains a hydrogen alpha to the —NOH moiety" means that the present dialkylhydroxylamines are not di-tert-alkylhydroxylamines.

The present dialkylhydroxylamine stabilizers are, for example, N,N-dihydrocarbylhydroxylamines wherein $R_1$ and $R_2$ are independently benzyl, methyl, ethyl, octyl, lauryl, dodecyl, tetradecyl, hexadecyl, heptadecyl or octadecyl, or wherein $R_1$ and $R_2$ are each the alkyl mixture found in hydrogenated tallow amine.

The present dialkylhydroxylamine stabilizers are, for example, N,N-dihydrocarbylhydroxylamines selected from the group consisting of N,N-dibenzylhydroxylamine, N,N-dimethylhydroxylamine, N,N-diethylhydroxylamine, N,N-bis(2-hydroxypropyl)hydroxyl-amine, N,N-bis(3-hydroxypropyl)hydroxylamine, N,N-bis(2-carboxyethyl)hydroxylamine, N,N-bis(benzylthiomethyl)hydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine, N,N-di(hydrogenated tallow)hydroxylamine.

For example, the present dialkylhydroxylamine stabilizers are N,N-diethylhydroxylamine, N,N-bis(2-hydroxypropyl)hydroxylamine, N,N-bis(3-hydroxypropyl)hydroxylamine or N,N-dibenzylhydroxylamine or the N,N-di(alkyl)hydroxylamine produced by the direct oxidation of N,N-di(hydrogenated tallow)amine. The last named dialkylhydroxylamine, that is N,N-di(hydrogenated tallow)hydroxylamine, is as prepared in the working Examples of U.S. Pat. No. 5,013,510.

The dialkylhydroxylamine stabilizer salts of formula V are inorganic or organic acid salts of the present dialkylhydroxylamine stabilizers of formula IV. For example, the dialkylhydroxylamine stabilizer salts are of the formula $$(R_1R_2N—OH).(HY) \quad (V)$$

where $R_1$ and $R_2$ are as defined for the dialkylhydroxylamine stabilizers, and HY is an inorganic or organic acid.

For example, Y is phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid (NTA), diethylenetriaminepentamethylenephosphonic acid (DTPMPA), hydroxyethylethylenediamine-triacetic acid (HEDTA), ethylenediaminetetraacetic acid (EDTA), diethylenetriaminepentaacetic acid (DTPA), diethylenediaminetetraacetic acid or of diethylenetriaminepentaacetic acid, an alkylsulfonate or an arylsulfonate.

For instance, when HY is hydrochloric acid, Y is chloride and the dialkylhydroxylamine salt is a dialkylhydroxylammonium chloride salt.

For example, Y is chloride, bisulfate, sulfate, phosphate, nitrate, ascorbate, formate, acetate, benzoate, oxalate, citrate, a carboxylate of ethylenediaminetetraacetic acid or of diethylenetriaminepentaacetic acid or polyacrylate, for instance Y is chloride, bisulfate or citrate.

For example, the present dialkylhydroxylamine stabilizer salts are salts of the specific dialkylhydroxylamine stabilizers disclosed above.

For example, the present dialkylhydroxylamine stabilizer salts are tris(N,N-diethylhydroxylammonium) citrate or tris (N,N-dibenzylhydroxylammonium) citrate.

Nitroxyls and sterically hindered hydroxylamines and their salts are compounds of formula I, II or III

(I)

(II)

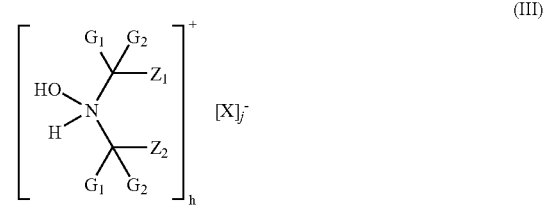

(III)

where $G_1$ and $G_2$ are independently alkyl of 1 to 4 carbon atoms or are together pentamethylene, $Z_1$ and $Z_2$ are each methyl, or $Z_1$ and $Z_2$ together form a linking moiety which may additionally be substituted by an ester, ether, hydroxy, oxo, cyanohydrin, amide, amino, carboxy or urethane group, X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and where the total charge of cations h is equal to the total charge of anions j.

For instance, X is chloride, bisulfite, bisulfate, sulfate, phosphate, nitrate, ascorbate, acetate, citrate or carboxylate of ethylenediaminetetraacetic acid or of diethylenetriaminepentaacetic acid; for instance X is bisulfate or citrate.

The nitroxyl, hydroxylamine and hydroxylamine salt compounds are for example of formulae A to EE and A* to EE*

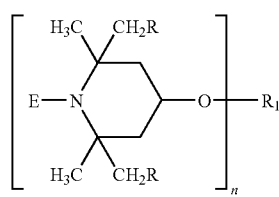
(A)

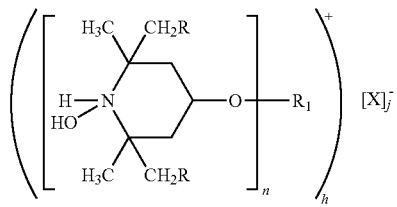
(A*)

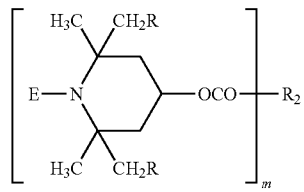
(B)

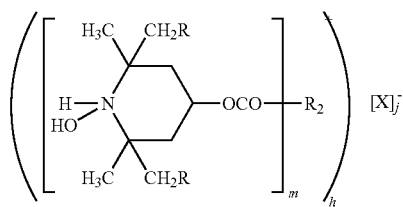
(B*)

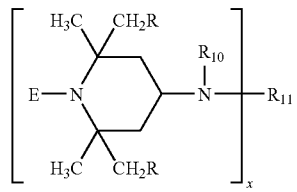
(C)

-continued

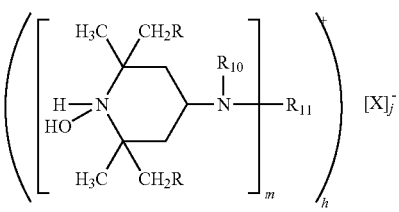
(C*)

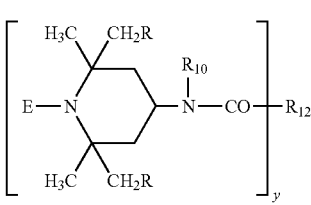
(D)

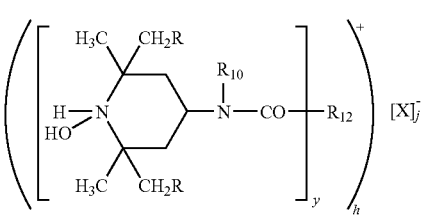
(D*)

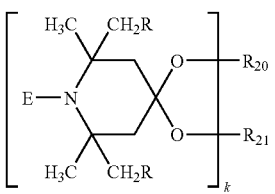
(E)

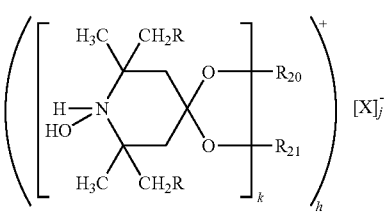
(E*)

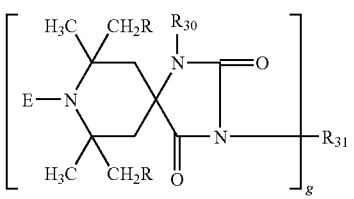
(F)

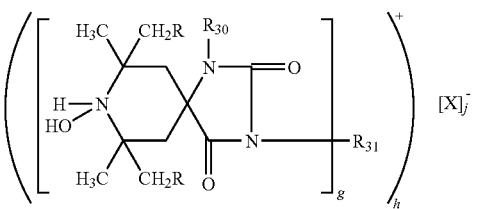
(F*)

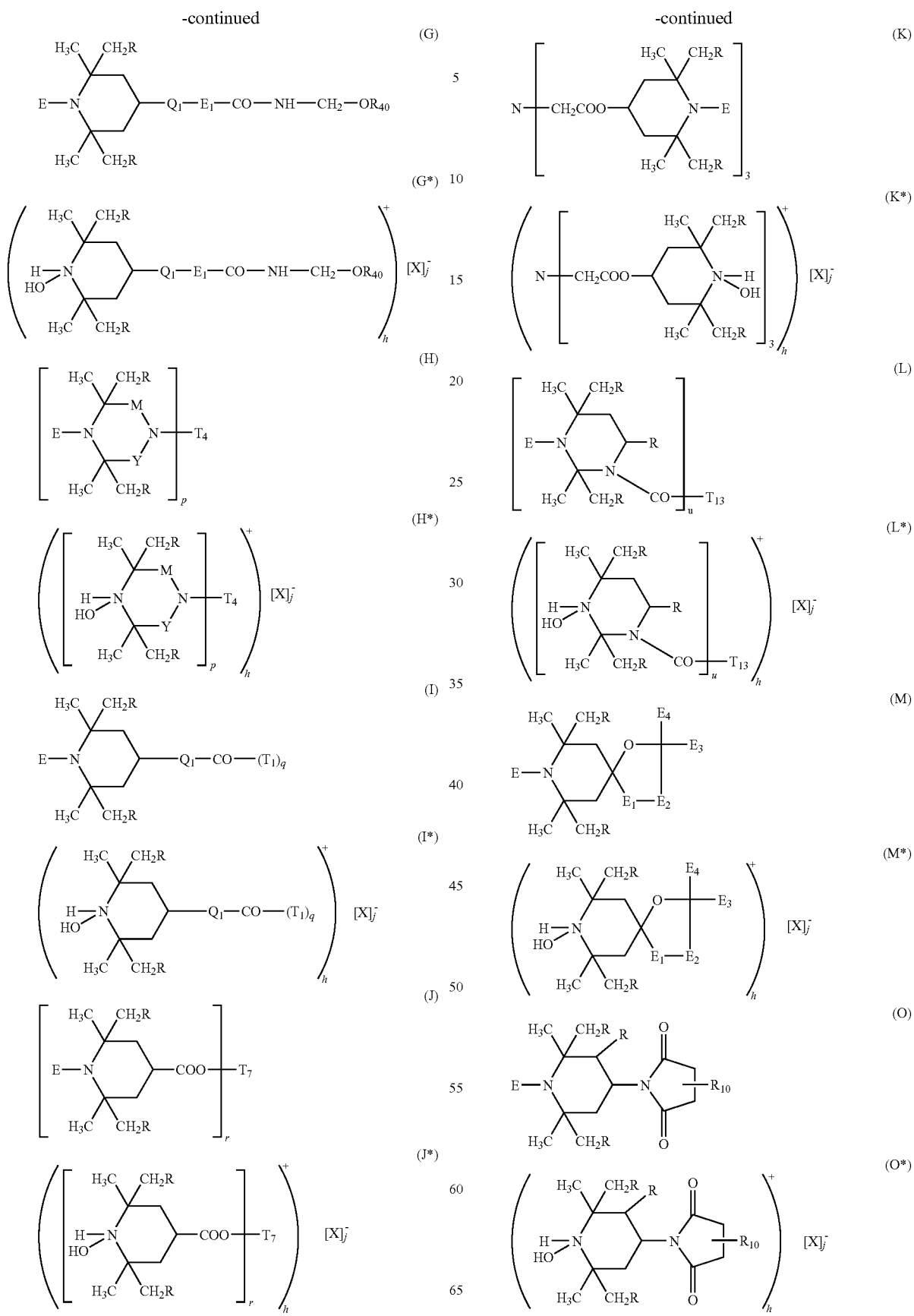

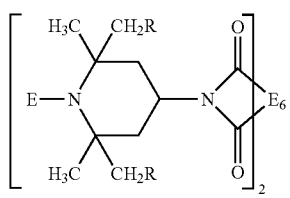 (P)
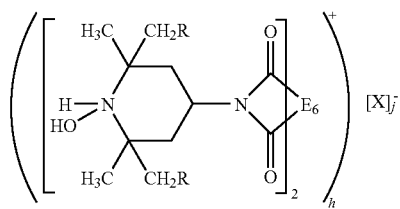 (P*)
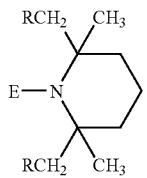 (Q)
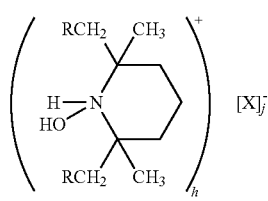 (Q*)
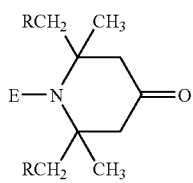 (R)
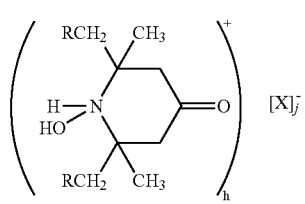 (R*)
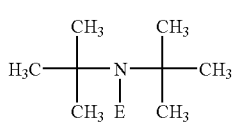 (S)
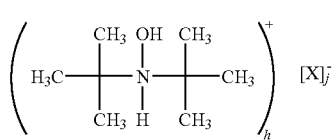 (S*)
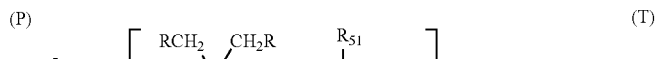 (T)
 (T*)
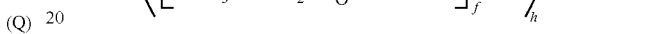 (U)
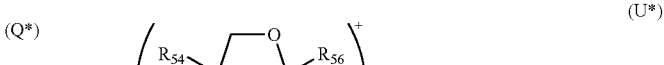 (U*)
 (V)
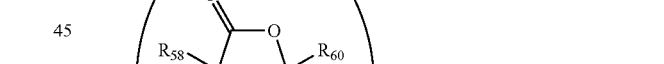 (V*)
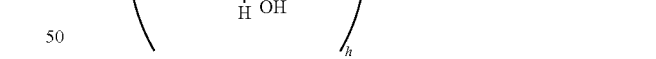 (W)
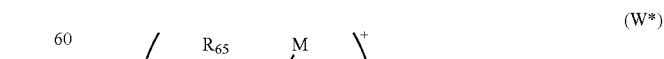 (W*)

-continued
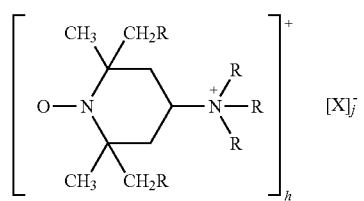 (X)
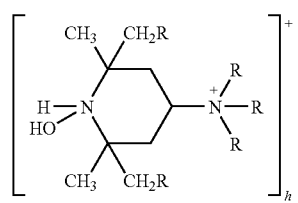 (X*)
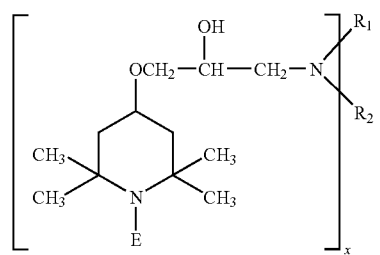 (Y)
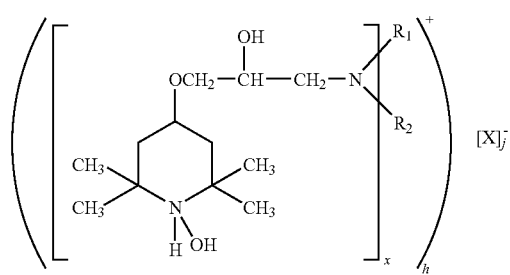 (Y*)
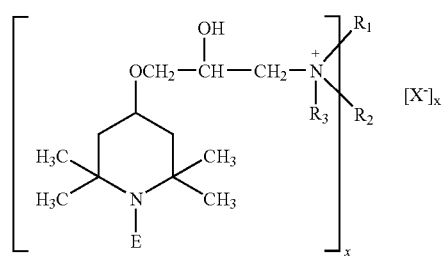 (Z)
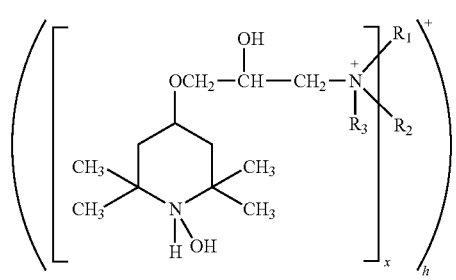 (Z*)
-continued
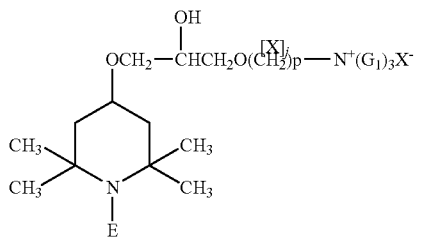 (AA)
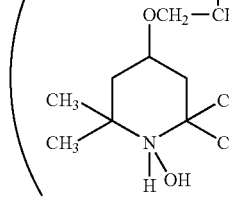 (AA*)
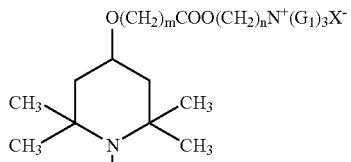 (BB)
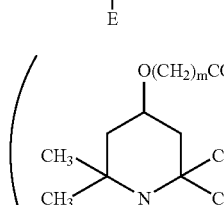 (BB*)
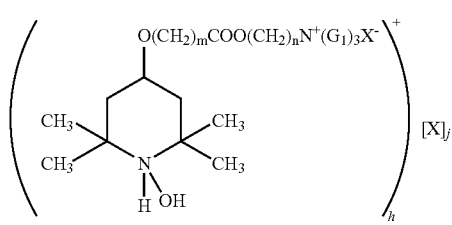 (CC)
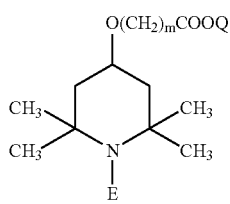 (CC*)
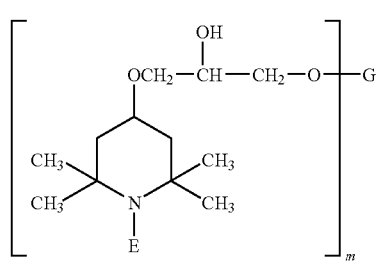 (DD)

-continued

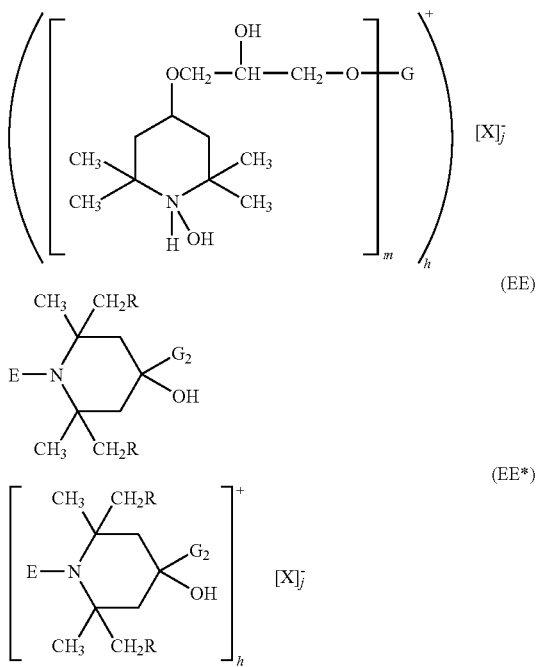

(DD*)

(EE)

(EE*)

wherein
E is oxyl or hydroxyl,
R is hydrogen or methyl, in formula A and A*,
n is 1 or 2,
when n is 1,
$R_1$ is hydrogen, alkyl of 1 to 18 carbon atoms, alkenyl of 2-18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or
$R_1$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$ M$^{n+}$ where n is 1-3 and M is a metal ion from the 1st, 2nd or 3rd group of the periodic table or is Zn, Cu, Ni or Co, or M is a group N$^{n+}$ (R$_2$)$_4$ where $R_2$ is alkyl of 1 to 8 carbon atoms or benzyl,
when n is 2,
$R_1$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula B and B*,
m is 1 to 4,
when m is 1,
$R_2$ is alkyl of 1 to 18 carbon atoms, alkyl of 3 to 18 carbon atoms interrupted by —COO—, or $R_2$ is —CH$_2$(OCH$_2$CH$_2$)$_n$ OCH$_3$ where n is 1 to 12, or
$R_2$ is cycloalkyl of 5 to 12 carbon atoms, aryl of 6 to 12 carbon atoms, or said aryl substituted by one to four alkyl groups of 1 to 4 carbon atoms, or $R_2$ is —NHR$_3$ where $R_3$ is alkyl of 1 to 18 carbon atoms, cycloalkyl of 5 to 12 carbon atoms, aryl of 6 to 12 carbon atoms, or said aryl substituted by one to four alkyl of 1 to 4 carbon atoms,
or $R_2$ is —N(R$_3$)$_2$ where $R_3$ is as defined above,
when m is 2,
$R_2$ is alkylene of 1 to 12 carbon atoms, alkenylene of 4 to 12 carbon atoms, xylylene, alkylene of 2 to 12 carbon atoms interrupted by —COO—, or $R_2$ is —CH$_2$(OCH$_2$CH$_2$)$_n$ OCH$_2$— where n is 1 to 12, or
$R_2$ is cycloalkylene of 5 to 12 carbon atoms, aralkylene of 7 to 15 carbon atoms or arylene of 6 to 12 carbon atoms, or
$R_2$ is —NHR$_4$NH— where $R_4$ is alkylene of 2 to 18 carbon atoms, cycloalkylene of 5 to 12 carbon atoms, aralkylene of 8 to 15 carbon atoms or arylene of 6 to 12 carbon atoms, or
$R_2$ is —N(R$_3$)R$_4$N(R$_3$)— where $R_3$ and $R_4$ are as defined above, or
$R_2$ is —CO— or —NH—CO—NH—,
when m is 3,
$R_2$ is alkanetriyl of 3 to 8 carbon atoms or benzenetriyl,
when m is 4,
$R_2$ is alkanetetrayl of 5 to 8 carbon atoms or benzenetetrayl, in formula C and C*,
$R_{10}$ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl,
x is 1 or 2,
when x is 1,
$R_{11}$ is hydrogen, alkyl of 1 to 18 carbon atoms, alkenyl of 2 to 18 carbon atoms, propargyl, glycidyl, alkyl of 2 to 50 carbon atoms interrupted by one to twenty oxygen atoms, said alkyl substituted by one to ten hydroxyl groups or both interrupted by said oxygen atoms and substituted by said hydroxyl groups, or
$R_{11}$ is alkyl of 1 to 4 carbon atoms substituted by a carboxy group or by —COOZ where Z is hydrogen, alkyl of 1 to 4 carbon atoms or phenyl, or where Z is said alkyl substituted by —(COO$^-$)$_n$M$^{n+}$ where n is 1-3 and M is a metal ion from the 1st, 2nd or 3rd group of the periodic table or is Zn, Cu, Ni or Co, or M is a group N$^{n+}$ (R$_2$)$_4$ where $R_2$ is hydrogen, alkyl of 1 to 8 carbon atoms or benzyl,
when x is 2,
$R_{11}$ is alkylene of 1 to 12 carbon atoms, alkenylene of 4 to 12 carbon atoms, xylylene or alkylene of 1 to 50 carbon atoms interrupted by one to twenty oxygen atoms, substituted by one to ten hydroxyl groups or both interrupted by said oxygen atoms and substituted by said hydroxyl groups, in formula D and D*,
$R_{10}$ is as defined above,
y is 1 to 4, and
$R_{12}$ is defined as $R_2$ above, in formula E and E*,
k is 1 or 2,
when k is 1,
$R_{20}$ and $R_{21}$ are independently alkyl of 1 to 12 carbon atoms, alkenyl of 2 to 12 carbon atoms or aralkyl of 7 to 15 carbon atoms, or $R_{20}$ is also hydrogen, or
$R_{20}$ and $R_{21}$ together are alkylene of 2 to 8 carbon atoms or said alkylene substituted by hydroxyl, or are acyloxy-alkylene of 4 to 22 carbon atoms,
when k is 2,
$R_{20}$ and $R_{21}$ are together (—CH$_2$)$_2$C(CH$_2$—)$_2$, in formula F and F*, $R_{30}$ is hydrogen, alkyl of 1 to 18 carbon atoms, benzyl, glycidyl, or alkoxyalkyl of 2 to 6 carbon atoms, g is 1 or 2, when g is 1, $R_{31}$ is defined as $R_1$ above when n is 1, when g is 2, $R_{31}$ is defined as $R_1$ above when n is 2, in formula G and G*, $Q_1$ is —$NR_{41}$— or —O—, $E_1$ is alkylene of 1 to 3 carbon atoms, or $E_1$ is —$CH_2$—CH($R_{42}$)—O— where $R_{42}$ is hydrogen, methyl or phenyl, or $E_1$ is —$(CH_2)_3$—NH— or $E_1$ is a direct bond, $R_{40}$ is hydrogen or alkyl of 1 to 18 carbon atoms, $R_{41}$ is hydrogen, alkyl of 1 to 18 carbon atoms, cycloalkyl of 5 to 12 carbon atoms, aralkyl of 7 to 15 carbon atoms, aryl of 6 to 10 carbon atoms, or $R_{41}$ is —$CH_2$—CH($R_{42}$)—OH where $R_{42}$ is as defined above, in formula H and H*, p is 1 or 2, $T_4$ is as defined for $R_{11}$ when x is 1 or 2, M and Y are independently methylene or carbonyl, for instance M is methylene and Y is carbonyl, in formula I and I*, this formula denotes a recurring structural unit of a polymer where $T_1$ is ethylene or 1,2-propylene or is the repeating structural unit derived from an alpha-olefin copolymer with an alkyl acrylate or methacrylate, and where q is 2 to 100, $Q_1$ is —$N(R_{41})$— or —O— where $R_{41}$ is as defined above, in formula J and J*, r is 1 or 2, $T_7$ is as defined for $R_1$ when n is 1 or 2 in formula A, for example $T_7$ is octamethylene when r is 2, in formula L and L*, u is 1 or 2, $T_{13}$ is as defined for $R_1$ when n is 1 or 2 in formula A, with the proviso that $T_{13}$ is not hydrogen when u is 1, in formula M and M*, $E_1$ and $E_2$, being different, each are —CO— or —$N(E_5)$— where $E_5$ is hydrogen, alkyl of 1 to 12 carbon atoms or alkoxycarbonylalkyl of 4 to 22 carbon atoms, for instance $E_1$ is —CO— and $E_2$ is —$N(E_5)$—, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by one to four alkyl of 1 to 4 carbon atoms, for example methyl, in formula O and O*, $R_{10}$ is as defined for $R_{10}$ in formula C, in formula P and P*, $E_6$ is an aliphatic or aromatic tetravalent radical, for example neopentanetetrayl or benzenetetrayl, in formula T and T*, $R_{51}$ is hydrogen, alkyl of 1 to 18 carbon atoms, cycloalkyl of 5 to 12 carbon atoms, or aryl of 6 to 10 carbon atoms, $R_{52}$ is hydrogen or alkyl of 1 to 18 carbon atoms, or $R_{51}$ and $R_{52}$ together of alkylene of 4 to 8 carbon atoms, f is 1 or 2, when f is 1, $R_{50}$ is as defined for $R_{11}$ in formula C when x is 1, or $R_{50}$ is —$(CH_2)_n COOR_{54}$ where z is 1 to 4 and $R_{54}$ is hydrogen or alkyl of 1 to 18 carbon atoms, or $R_{54}$ is a metal ion from the 1st, 2nd or 3rd group of the periodic table or a group —$N(R_{55})_4$ where $R_{55}$ is hydrogen, alkyl of 1 to 12 carbon atoms or benzyl, when f is 2, $R_{50}$ is as defined for $R_{11}$ in formula C when x is 2, in formula U and U*, $R_{53}$, $R_{54}$, $R_{55}$ and $R_{56}$ are independently alkyl of 1 to 4 carbon atoms or are together pentamethylene.

in formula V and V*, $R_{57}$, $R_{58}$, $R_{59}$ and $R_{60}$ are independently alkyl of 1 to 4 carbon atoms or are together pentamethylene, in formula W and W*, $R_{61}$, $R_{62}$, $R_{63}$ and $R_{64}$ are independently alkyl of 1 to 4 carbon atoms or are together pentamethylene, $R_{65}$ is alkyl of 1 to 5 carbon atoms, M is hydrogen or oxygen, wherein in formulas X to CC and X* to CC* n is 2 to 3, $G_1$ is hydrogen, methyl, ethyl, butyl or benzyl, m is 1 to 4, x is 1 to 4, when x is 1, $R_1$ and $R_2$ are independently alkyl of 1 to 18 carbon atoms, said alkyl interrupted by one to five oxygen atoms, said alkyl substituted by 1 to 5 hydroxyl groups or said alkyl both interrupted by said oxygen atoms and substituted by said hydroxyl groups; cycloalkyl of 5 to 12 carbon atoms, aralkyl of 7 to 15 carbon atoms, aryl of 6 to 10 carbon atoms or said aryl substituted by one to three alkyl of 1 to 8 carbon atoms, or $R_1$ is also hydrogen, or $R_1$ and $R_2$ are together tetramethylene, pentamethylene, hexamethylene or 3-oxapentamethylene, when x is 2, $R_1$ is hydrogen, alkyl of 1 to 8 carbon atoms, said alkyl interrupted by one or two oxygen atoms, said alkyl substituted by a hydroxyl group, or said alkyl both interrupted by one or two oxygen atoms and substituted by a hydroxyl group, $R_2$ is alkylene of 2 to 18 carbon atoms, said alkylene interrupted by one to five oxygen atoms, said alkylene substituted by 1 to 5 hydroxyl groups or said alkylene both interrupted by said oxygen atoms and substituted by said hydroxyl groups; o-, m- or p-phenylene or said phenylene substituted by one or two alkyl of 1 to 4 carbon atoms, or $R_2$ is —$(CH_2)_k O[(CH_2)_k O]_h (CH_2)_k$— where k is 2 to 4 and h is 1 to 40, or $R_1$ and $R_2$ together with the two N atoms to which they are attached are piperazin-1,4-diyl, when x is 3, $R_1$ is hydrogen, $R_2$ is alkylene of 4 to 8 carbon atoms interrupted by one nitrogen atom, when x is 4, $R_1$ is hydrogen, $R_2$ is alkylene of 6 to 12 carbon atoms interrupted by two nitrogen atoms, $R_3$ is hydrogen, alkyl of 1 to 8 carbon atoms, said alkyl interrupted by one or two oxygen atoms, said alkyl substituted by a hydroxyl group, or both interrupted by one or two oxygen atoms and substituted by a hydroxyl group, p is 2 or 3, and Q is an alkali metal salt, ammonium or $N^+(G_1)_4$, in formula DD and DD* m is 2 or 3, when m is 2, G is —(CH$_2$CHR—O)$_r$CH$_2$CHR—, where r is 0 to 3, and R is hydrogen or methyl, and when m is 3, G is glyceryl, in formula EE and EE*

G$_2$ is —CN, —CONH$_2$ or —COOG$_3$ where G$_3$ is hydrogen, alkyl of 1 to 18 carbon atoms or phenyl, X is an inorganic or organic anion, such as phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate, and where the total charge of cations h is equal to the total charge of anions j.

For example, the compounds of component (iii) are those of formulas A, A*, B, B*, C, C*, D, D*, Q, Q*, R, R*, S, S*, X, X*, Y, Y*, Z and Z*, wherein, R is hydrogen, and in formula A and A* n is 1 or 2, when n is 1,

R$_1$ is hydrogen, alkyl of 1 to 6 carbon atoms, alkenyl of 2-6 carbon atoms, propargyl, glycidyl, alkyl of 2 to 20 carbon atoms interrupted by one to ten oxygen atoms, said alkyl substituted by one to five hydroxyl groups or both interrupted by said oxygen atoms and substituted by said hydroxyl groups, or R$_1$ is alkyl of 1 to 4 carbon atoms substituted by a carboxy group or by —COOZ where Z is hydrogen or alkyl of 1 to 4 carbon atoms, when n is 2, R$_1$ is alkylene of 1 to 8 carbon atoms, alkenylene of 4 to 8 carbon atoms, alkylene of 1 to 20 carbon atoms interrupted by one to ten oxygen atoms, substituted by one to five hydroxyl groups or both interrupted by said oxygen atoms and substituted by said hydroxyl groups, in formula B and B* m is 1 or 2 when m is 1, R$_2$ is alkyl of 1 to 4 carbon atoms or R$_2$ is CH$_2$(OCH$_2$CH$_2$)$_n$OCH$_3$ where n is 1 to 12, or R$_2$ is phenyl, or said phenyl substituted by one to three methyl groups, or R$_2$ is —NHR$_3$ where R$_3$ is alkyl of 1 to 4 carbon atoms or phenyl, or said phenyl substituted by one or two methyl groups, when m is 2, R$_2$ is alkylene of 1 to 8 carbon atoms, alkenylene of 4 to 8 carbon atoms, or R$_2$ is —CH$_2$(OCH$_2$CH$_2$)$_n$OCH$_2$— where n is 1 to 12, or R$_2$ is NHR$_4$NH where R$_4$ is of 2 to 6 carbon atoms, aralkylene of 8 to 15 carbon atoms or arylene of 6 to 12 carbon atoms, or R$_2$ is —CO— or —NH-CONH, in formula C and C*, R$_{10}$ is hydrogen or, alkanoyl of 1 to 3 carbon atoms, x is 1 or 2, when x is 1, R$_{11}$ is hydrogen, alkyl of 1 to 6 carbon atoms or glycidyl, or R$_{11}$ is alkyl of 1 to 4 carbon atoms substituted by a carboxy group or by COOZ where Z is hydrogen or alkyl of 1 to 4 carbon atoms, when x is 2, R$_{11}$ is alkylene of 1 to 6 carbon atoms, in formula D and D*, R$_{10}$ is hydrogen, y is 1 or 2, R$_{12}$ is defined as R$_2$ above, in formula Y, Y*, Z and Z*, x is 1 or 2, when x is 1, R$_1$ and R$_2$ are independently alkyl of 1 to 4 carbon atoms, or R$_1$ and R$_2$ are together tetramethylene, or pentamethylene, or R$_2$ is hydrogen or alkyl of 1 to 4 carbon atoms, said alkyl group substituted by a hydroxyl group, when x is 2, R$_1$ is hydrogen, alkyl of 1 to 4 carbon atoms, said alkyl substituted by a hydroxyl group, R$_2$ is alkylene of 2 to 6 carbon atoms, R$_3$ is as defined above.

For instance, the compounds of component (b) are those of formulas A, A*, B, B*, C, C*, D, D*, Q, Q*, R and R*, wherein R is hydrogen, in formula A and A*, h is 1, R$_1$ is hydrogen, alkyl of 1 to 4 carbon atoms, glycidyl, alkyl of 2 to 4 carbon atoms interrupted by one or two oxygen atoms, said alkyl substituted by one or two hydroxyl groups or both interrupted by said oxygen atoms and substituted by said hydroxyl groups, or R$_1$ is alkyl of 1 to 4 carbon atoms substituted by —COOZ where Z is hydrogen or alkyl of 1 to 4 carbon atoms, in formula B and B*, m is 1 or 2, when m is 1, R$_2$ is alkyl of 1 to 4 carbon atoms or R$_2$ is CH$_2$(OCH$_2$CH$_2$)$_n$OCH$_3$ where n is 1 to 4, when m is 2, R$_2$ is alkylene of 1 to 8 carbon atoms, in formula C and C*, R$_{10}$ is hydrogen or alkanoyl of 1 or 2 carbon atoms, x is 1 or 2, when x is 1, R$_{11}$ is hydrogen, alkyl of 1 to 4 carbon atoms or glycidyl, or R$_{11}$ is alkyl of 1 to 4 carbon atoms substituted by COOZ where Z is hydrogen or alkyl of 1 to 4 carbon atoms, when x is 2, R$_{11}$ is alkylene of 1 to 6 carbon atoms, in formula D and D*, R$_{10}$ is hydrogen, y is 1 or 2, R$_{12}$ is defined as R$_2$ above.

For instance, the nitroxyl, hydroxylamine and hydroxylamine salt compounds of formula I, II and III are selected from bis(1-oxyl-2,2-6-6-tetramethylpiperidin-4-yl)sebacate;
bis(1-hydroxy-2,2-6-6-tetramethylpiperidin-4-yl)sebacate;
1-hydroxy-2,2-6-6-tetramethyl-4-acetoxypiperidinium citrate;
1-oxyl-2,2,6,6-tetramethyl-4-acetamidopiperidine;
1-hydroxy-2,2,6,6-tetramethyl-4-acetamidopiperidine;
1-hydroxy-2,2,6,6-tetramethyl-4-acetamidopiperidinium bisulfate;
1-oxyl-2,2,6,6-tetramethyl-4-oxo-piperidine;
1-hydroxy-2,2,6,6-tetramethyl-4-oxo-piperidine;
1-hydroxy-2,2,6,6-tetramethyl-4-oxo-piperidinium acetate;
1-oxyl-2,2,6,6-tetramethyl-4-methoxy-piperidine;
1-hydroxy-2,2,6,6-tetramethyl-4-methoxy-piperidine;
1-hydroxyl-2,2,6,6-tetramethyl-4-methoxy-piperidinium acetate;
1-oxyl-2,2,6,6-tetramethyl-4-acetoxypiperidine;
1-hydroxy-2,2,6,6-tetramethyl-4-acetoxypiperidine;
1-oxyl-2,2,6,6-tetramethyl-4-propoxy-piperidine;
1-hydroxy-2,2,6,6-tetramethyl-4-propoxy-piperidinium acetate;
1-hydroxy-2,2,6,6-tetramethyl-4-propoxy-piperidine;
1-oxyl-2,2,6,6-tetramethyl-4-(2-hydroxy-4-oxapentoxy)piperidine;

1-hydroxy-2,2,6,6-tetramethyl-4-(2-hydroxy-4-oxapentoxy) piperidinium acetate;
1-oxyl-2,2,6,6-tetramethyl-4-hydroxypiperidine;
1-hydroxy-2,2,6,6-tetramethyl-4-hydroxypiperidine;
1-hydroxy-2,2,6,6-tetramethyl-4-hydroxypiperidinium chloride;
1-hydroxy-2,2,6,6-tetramethyl-4-hydroxypiperidinium acetate;
1-hydroxy-2,2,6,6-tetramethyl-4-hydroxypiperidinium bisulfate;
1-hydroxy-2,2,6,6-tetramethyl-4-hydroxypiperidinium citrate;
bis(1-hydroxy-2,2,6,6-tetramethyl-4-hydroxypiperidinium) citrate;
tris(1-hydroxy-2,2,6,6-tetramethyl-4-hydroxypiperidinium) citrate.
tetra(1-hydroxy-2,2,6,6-tetramethyl-4-hydroxypiperidinium)ethylenediaminetetraacetate;
tetra(1-hydroxy-2,2,6,6-tetramethyl-4-acetamidopiperidinium)ethylenediaminetetraacetate;
tetra(1-hydroxy-2,2,6,6-tetramethyl-4-oxopiperidinium)ethylenediaminetetraacetate;
penta(1-hydroxy-2,2,6,6-tetramethyl-4-hydroxypiperidinium) diethylenetriaminepentaacetate;
penta(1-hydroxy-2,2,6,6-tetramethyl-4-acetamidopiperidinium)diethylenetriaminepentaacetate;
penta(1-hydroxy-2,2,6,6-tetramethyl-4-oxopiperidinium)diethylenetriaminepentaacetate;
tri(1-hydroxy-2,2,6,6-tetramethyl-4-hydroxypiperidinium) nitrilotriacetate;
tri(1-hydroxy-2,2,6,6-tetramethyl-4-acetamidopiperidinium)nitrilotriacetate;
tri(1-hydroxy-2,2,6,6-tetramethyl-4-oxopiperidinium)nitrilotriacetate;
penta(1-hydroxy-2,2,6,6-tetramethyl-4-hydroxypiperidinium)diethylenetriaminepentamethylenephosphonate;
penta(1-hydroxy-2,2,6,6-tetramethyl-4-acetamidopiperidinium)diethylenetriaminepentamethylenephosphonate; and
penta(1-hydroxy-2,2,6,6-tetramethyl-4-oxopiperidinium)diethylenetriaminepentamethylenephosphonate.

For example, the compounds of formula I, II and III are selected from the group consisting of
bis(1-oxyl-2,2-6-6-tetramethylpiperidin-4-yl)sebacate;
1-oxyl-2,2,6,6-tetramethyl-4-acetamidopiperidine;
1-oxyl-2,2,6,6-tetramethyl-4-oxo-piperidine;
1-oxyl-2,2,6,6-tetramethyl-4-methoxy-piperidine;
1-oxyl-2,2,6,6-tetramethyl-4-acetoxypiperidine;
1-oxyl-2,2,6,6-tetramethyl-4-propoxy-piperidine;
1-oxyl-2,2,6,6-tetramethyl-4-(2-hydroxy-4-oxapentoxy)piperidine;
1-oxyl-2,2,6,6-tetramethyl-4-hydroxypiperidine;

For example, the compounds of formula I, II and III are selected from the group consisting of
bis(1-hydroxy-2,2-6-6-tetramethylpiperidin-4-yl)sebacate;
1-hydroxy-2,2,6,6-tetramethyl-4-acetamidopiperidine;
1-hydroxy-2,2,6,6-tetramethyl-4-oxo-piperidine;
1-hydroxy-2,2,6,6-tetramethyl-4-methoxy-piperidine;
1-hydroxy-2,2,6,6-tetramethyl-4-acetoxypiperidine;
1-hydroxy-2,2,6,6-tetramethyl-4-propoxy-piperidine;
1-hydroxy-2,2,6,6-tetramethyl-4-hydroxypiperidine;

For example, the compounds of formula I, II and III are selected from the group consisting of
1-hydroxy-2,2-6-6-tetramethyl-4-acetoxypiperidinium citrate;
bis(1-hydroxy-2,2,6,6-tetramethyl-4-acetoxypiperidinium) citrate;
tris(1-hydroxy-2,2,6,6-tetramethyl-4-acetoxypiperidinium) citrate;
1-hydroxy-2,2,6,6-tetramethyl-4-acetamidopiperidinium bisulfate;
1-hydroxy-2,2,6,6-tetramethyl-4-oxo-piperidinium acetate;
1-hydroxy-2,2,6,6-tetramethyl-4-oxo-piperidinium citrate;
bis(1-hydroxy-2,2,6,6-tetramethyl-4-oxo-piperidinium) citrate;
tris(1-hydroxy-2,2,6,6-tetramethyl-4-oxo-piperidinium) citrate;
1-hydroxyl-2,2,6,6-tetramethyl-4-methoxy-piperidinium acetate;
1-hydroxy-2,2,6,6-tetramethyl-4-propoxy-piperidinium acetate;
1-hydroxy-2,2,6,6-tetramethyl-4-(2-hydroxy-4-oxapentoxy) piperidinium acetate;
1-hydroxy-2,2,6,6-tetramethyl-4-hydroxypiperidinium chloride;
1-hydroxy-2,2,6,6-tetramethyl-4-hydroxypiperidinium acetate;
1-hydroxy-2,2,6,6-tetramethyl-4-hydroxypiperidinium bisulfate;
1-hydroxy-2,2,6,6-tetramethyl-4-hydroxypiperidinium citrate;
bis(1-hydroxy-2,2,6,6-tetramethyl-4-hydroxypiperidinium) citrate;
tris(1-hydroxy-2,2,6,6-tetramethyl-4-hydroxypiperidinium) citrate;
1-hydroxy-2,2,6,6-tetramethyl-4-acetamidopiperidinium citrate;
bis(1-hydroxy-2,2,6,6-tetramethyl-4-acetamidopiperidinium) citrate;
tris(1-hydroxy-2,2,6,6-tetramethyl-4-acetamidopiperidinium) citrate;
tetra(1-hydroxy-2,2,6,6-tetramethyl-4-hydroxypiperidinium)ethylenediaminetetraacetate;
tetra(1-hydroxy-2,2,6,6-tetramethyl-4-acetamidopiperidinium)ethylenediaminetetraacetate;
tetra(1-hydroxy-2,2,6,6-tetramethyl-4-oxopiperidinium)ethylenediaminetetraacetate;
penta(1-hydroxy-2,2,6,6-tetramethyl-4-hydroxypiperidinium)diethylenetriaminepentaacetate;
penta(1-hydroxy-2,2,6,6-tetramethyl-4-acetamidopiperidinium)diethylenetriaminepentaacetate;
penta(1-hydroxy-2,2,6,6-tetramethyl-4-oxopiperidinium)diethylenetriaminepentaacetate;
tri(1-hydroxy-2,2,6,6-tetramethyl-4-hydroxypiperidinium) nitrilotriacetate;
tri(1-hydroxy-2,2,6,6-tetramethyl-4-acetamidopiperidinium)nitrilotriacetate;
tri(1-hydroxy-2,2,6,6-tetramethyl-4-oxopiperidinium)nitrilotriacetate;
penta(1-hydroxy-2,2,6,6-tetramethyl-4-hydroxypiperidinium)diethylenetriaminepentamethylenephosphonate;
penta(1-hydroxy-2,2,6,6-tetramethyl-4-acetamidopiperidinium)diethylenetriaminepentamethylenephosphonate; and
penta(1-hydroxy-2,2,6,6-tetramethyl-4-oxopiperidinium)diethylenetriaminepentamethylenephosphonate.

For Example, the compounds of formula I, II and III are selected from the group consisting of
1-hydroxy-2,2,6,6-tetramethyl-4-hydroxypiperidinium citrate;
bis(1-hydroxy-2,2,6,6-tetramethyl-4-hydroxypiperidinium) citrate;
tris(1-hydroxy-2,2,6,6-tetramethyl-4-hydroxypiperidinium) citrate;

1-hydroxy-2,2,6,6-tetramethyl-4-hydroxypiperidinium DTPA;
bis(1-hydroxy-2,2,6,6-tetramethyl-4-hydroxypiperidinium) DTPA;
tris(1-hydroxy-2,2,6,6-tetramethyl-4-hydroxypiperidinium) DTPA;
tetrakis(1-hydroxy-2,2,6,6-tetramethyl-4-hydroxypiperidinium) DTPA;
pentakis(1-hydroxy-2,2,6,6-tetramethyl-4-hydroxypiperidinium) DTPA;
1-hydroxy-2,2,6,6-tetramethyl-4-hydroxypiperidinium EDTA;
bis(1-hydroxy-2,2,6,6-tetramethyl-4-hydroxypiperidinium) EDTA;
tris(1-hydroxy-2,2,6,6-tetramethyl-4-hydroxypiperidinium) EDTA;
tetrakis(1-hydroxy-2,2,6,6-tetramethyl-4-hydroxypiperidinium) EDTA;
1-hydroxy-2,2,6,6-tetramethyl-4-oxo-piperidinium DTPA;
bis(1-hydroxy-2,2,6,6-tetramethyl-4-oxo-piperidinium) DTPA;
tris(1-hydroxy-2,2,6,6-tetramethyl-4-oxo-piperidinium) DTPA;
tetrakis(1-hydroxy-2,2,6,6-tetramethyl-4-oxo-piperidinium) DTPA;
pentakis(1-hydroxy-2,2,6,6-tetramethyl-4-oxo-piperidinium) DTPA;
1-hydroxy-2,2,6,6-tetramethyl-4-oxo-piperidinium EDTA;
bis(1-hydroxy-2,2,6,6-tetramethyl-4-oxo-piperidinium) EDTA;
tris(1-hydroxy-2,2,6,6-tetramethyl-4-oxo-piperidinium) EDTA;
tetrakis(1-hydroxy-2,2,6,6-tetramethyl-4-oxo-piperidinium) EDTA;
1-hydroxy-2,2,6,6-tetramethyl-4-acetamidopiperidinium DTPA;
bis(1-hydroxy-2,2,6,6-tetramethyl-4-acetamidopiperidinium) DTPA;
tris(1-hydroxy-2,2,6,6-tetramethyl-4-acetamidopiperidinium) DTPA;
tetrakis(1-hydroxy-2,2,6,6-tetramethyl-4-acetamidopiperidinium) DTPA;
pentakis(1-hydroxy-2,2,6,6-tetramethyl-4-acetamidopiperidinium) DTPA;
1-hydroxy-2,2,6,6-tetramethyl-4-acetamidopiperidinium EDTA;
bis(1-hydroxy-2,2,6,6-tetramethyl-4-acetamidopiperidinium) EDTA;
tris(1-hydroxy-2,2,6,6-tetramethyl-4-acetamidopiperidinium) EDTA;
tetrakis(1-hydroxy-2,2,6,6-tetramethyl-4-hydroxypiperidinium) EDTA;
1-hydroxy-2,2,6,6-tetramethyl-4-acetoxypiperidinium citrate;
bis(1-hydroxy-2,2,6,6-tetramethyl-4-acetoxypiperidinium) citrate;
tris(1-hydroxy-2,2,6,6-tetramethyl-4-acetoxypiperidinium) citrate;
1-hydroxy-2,2,6,6-tetramethyl-4-acetoxypiperidinium DTPA;
bis(1-hydroxy-2,2,6,6-tetramethyl-4-acetoxypiperidinium) DTPA;
tris(1-hydroxy-2,2,6,6-tetramethyl-4-acetoxypiperidinium) DTPA;
tetrakis(1-hydroxy-2,2,6,6-tetramethyl-4-acetoxypiperidinium) DTPA;
pentakis(1-hydroxy-2,2,6,6-tetramethyl-4-acetoxypiperidinium) DTPA;
1-hydroxy-2,2,6,6-tetramethyl-4-acetoxypiperidinium EDTA;
bis(1-hydroxy-2,2,6,6-tetramethyl-4-acetoxypiperidinium) EDTA;
tris(1-hydroxy-2,2,6,6-tetramethyl-4-acetoxypiperidinium) EDTA and
tetrakis(1-hydroxy-2,2,6,6-tetramethyl-4-acetoxypiperidinium) EDTA.

The above named counter-ions are ethylenediaminetetraacetic acid (EDTA), diethylene-triaminepentaacetic acid (DTPA), hydroxyethylethylenediaminetriacetic acid (HEDTA), nitrilotriacetic acid (NTA) or diethylenetriaminepentamethylenephosphonic acid (DTPMPA).

For example, the compounds of formula I, II and III are selected from the group consisting of
1-hydroxy-2,2-6-6-tetramethyl-4-acetoxypiperidinium citrate;
1-hydroxy-2,2,6,6-tetramethyl-4-acetamidopiperidinium bisulfate;
1-hydroxy-2,2,6,6-tetramethyl-4-oxo-piperidinium acetate;
1-hydroxyl-2,2,6,6-tetramethyl-4-methoxy-piperidinium acetate;
1-hydroxy-2,2,6,6-tetramethyl-4-propoxy-piperidinium acetate;
1-hydroxy-2,2,6,6-tetramethyl-4-(2-hydroxy-4-oxapentoxy) piperidinium acetate;
1-hydroxy-2,2,6,6-tetramethyl-4-hydroxypiperidinium chloride;
1-hydroxy-2,2,6,6-tetramethyl-4-hydroxypiperidinium acetate;
1-hydroxy-2,2,6,6-tetramethyl-4-hydroxypiperidinium bisulfate;
1-hydroxy-2,2,6,6-tetramethyl-4-hydroxypiperidinium citrate;
bis(1-hydroxy-2,2,6,6-tetramethyl-4-hydroxypiperidinium) citrate;
tris(1-hydroxy-2,2,6,6-tetramethyl-4-hydroxypiperidinium) citrate;

The present stabilizers are incorporated by dissolution using standard techniques, where required at elevated temperature.

The hindered nitroxyls, hydroxylamines or hydroxylamine salts of this invention may be present in very low amounts, for example as low as 0.001% by weight, based on the weight of the solvent, but are also present in amounts of from about 0.01% to about 10% by weight, based on the weight of the solvent. The UVAs may be present in amounts as high as about 25% by weight, based on the weight of the solvent, but generally are present in amounts of about 0.1% to about 20%, about 0.1% to about 15%; more typically about 1% to about 10%, or about 3% to about 6% by weight, based on the weight of the solvent.

The UVAs and hydroxylamines or hydroxylamine salts of this invention, in total, are present for example from about 0.05% to about 30% by weight, based on the weight of the solvent, for example from about 0.1% to about 15%, or from about 0.2% to about 10% by weight, or from about 1% to about 5% by weight.

The nitroxyl, hydroxylamine or hydroxylamine salt component may be linked as through a covalent bond to a moiety comprising the UVA component.

The term "effective amount" in reference to the additives is that amount that results in the desired effect regarding light stability and yellowing.

The present compositions may comprise further additives, for example hindered amine light stabilizers (HALS). are disclosed for example in U.S. Pat. Nos. 3,640,928; 3,992,390; 5,204,473; 5,980,783; 6,046,304; 6,297,299; 5,844,026 and 6,271,377; 5,980,783; 6,046,304 and 6,297,299, the disclosures of which are hereby incorporated by reference. The HALS included in the composition may be any such additives, or mixture of HALS, many of which are well known in the art. The HALS may also be oligomeric or polymeric.

The present invention also pertains to a method of stabilizing an electroactive composition which comprises incorporating therein at least one compound of the formulae (I), (II), (III), (IV) or (V).

EXAMPLES

The following working examples help to illustrate the effectiveness of compositions of the present invention in preventing the yellowing of UV stabilized solvent systems useful in electroactive devices.

Solutions are prepared in air using standard conditions, heating is employed when necessary. UV exposures are run in an Atlas 4,000 xenon weatherometer under interior automotive conditions J 1885. Yellowing is determined either by direct observation or via Gardner color measurements. The Gardner color number is defined in DIN ISO 4630, a lower number correlates with less color. The UVAs are either commercial products or prepared as in the patents referenced Percentages are in weight percent unless indicated otherwise.

Example 1

Solutions of octyl 3-(benzotriazol-2-yl)-5-tert-butyl-4-hydroxyhydrocinnamate in propylene carbonate are prepared, 3.8 weight % UVA based on total weight of solvent. 1-hydroxy-2,2,6,6-tetramethyl-4-hydroxypiperidinium citrate is added at 0.2 and 0.4 weight % based on total weight of solvent. The resulting solutions are exposed in an Atlas 4,000 xenon weatherometer as above and the resulting color measured at the total irradiance indicated and compared to a solution without the hydroxylamine citrate.

| Concentration of hydroxylamine citrate | Gardner Number | | | |
| --- | --- | --- | --- | --- |
| | 128 hrs | 256 hrs | 512 hrs | 640 hrs |
| — | 1.3 | 3.0 | 4.5 | 5.1 |
| 0.2% | 0.7 | 0.6 | 0.5 | 0.4 |
| 0.4% | 0.6 | 0.7 | 0.7 | — |

What is claimed is:

1. An electroactive device which device comprises a medium in the electroactive device, which medium composition comprises
   i) one or more solvents suitable as a medium in the electroactive device,
   ii) an effective amount of one or more additive compounds selected from the group consisting of ultraviolet light absorbers, and
   iii) an effective amount of one or more additive compounds selected from the group consisting of nitroxyls, hydroxyl amines and hydroxyl amine salts,
wherein at least one of the one or more nitroxyls, hydroxyl amines and hydroxyl amine salts of component (iii) is a compound of formula I, II or III

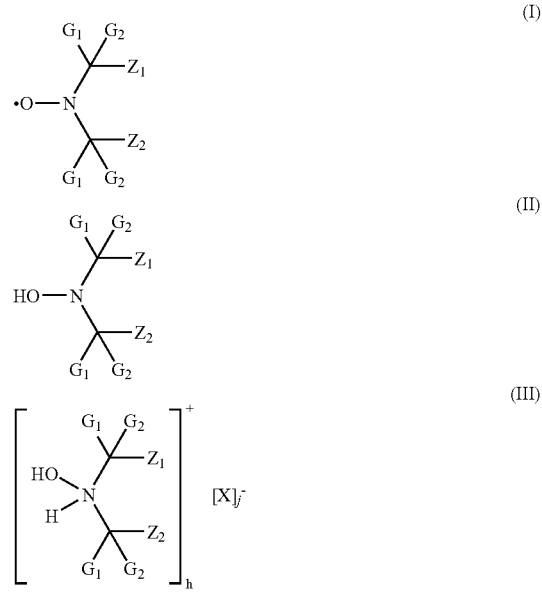

where
$G_1$ and $G_2$ are independently alkyl of 1 to 4 carbon atoms or are together pentamethylene, $Z_1$ and $Z_2$ are each methyl, or $Z_1$ and $Z_2$ together form a linking moiety which may additionally be substituted by an ester, ether, hydroxy, oxo, cyanohydrin, amide, amino, carboxy or urethane group, X is an inorganic or organic anion, and where the total charge of cations h is equal to the total charge of anions j, wherein the electroactive device further contains a pair of electrodes and at least one compound or material that changes transmittance upon or after application of an electric stimulus.

2. The device according to claim 1, wherein at least one of the one or more solvents is selected from the group consisting of sulfones, amides, sulfoxides, ethers, polyethers, alcohols, polyols, nitriles, ketones, aldehydes, carboxylic acids, cyclic esters, cyclic carbonates, glycidyl ether carbonates and silicon/polyol co-polymers.

3. The device according to claim 2, wherein at least one of the one or more solvents is selected from the group consisting of 3-methylsulfolane, tetramethylene sulfone, N,N-dimethylformamide, dimethyl sulfoxide, tetraglyme, methanol, ethanol, ethoxyethanol, acetonitrile, glutaronitrile, 3-hydroxypropionitrile, methoxypropionitrile, 3-ethoxypropionitrile 2-methylglutaronitrile, cyanoethyl sucrose, acetone, methyl ethyl ketone, methyl amyl ketone, cyclopentanone, cyclohexanone, benzoyl acetone, 4-hydroxy-4-methyl-2-pentanone, acetophenone, acetic acid, beta-propiolactone, 2-acetylbutyrolactone, gamma-butyrolactone, gamma-valerolactone, 4-ethenyl-1,3-dioxalane-2-one, propylene carbonate, ethylene carbonate and 1,2-butylene carbonate.

4. The device according to claim 3, wherein at least one of the one or more solvents is selected from the group consisting of 3-methylsulfolane, tetramethylene sulfone, tetraglyme, acetonitrile, glutaronitrile, 3-hydroxypropionitrile, methoxypropionitrile, 3-ethoxypropionitrile, 2-methylglutaronitrile, acetone, methyl ethyl ketone, methyl amyl ketone, cyclopentanone, cyclohexanone, 4-ethenyl-1,3-dioxalane-2-one, propylene carbonate, ethylene carbonate and 1,2-butylene carbonate.

5. The device according to claim 1, wherein at least one of the one or more ultraviolet light absorbers is selected from the group consisting of hydroxyphenylbenzotriazoles, benzophenones, and tris-aryl-s-triazines.

6. The device according to claim 1, wherein at least one component that is selected from nitroxyls, hydroxyl amines and hydroxyl amines salts is a nitroxyl.

7. The device according to claim 1, wherein at least one component that is selected from nitroxyls, hydroxyl amines and hydroxyl amine salts is a hydroxyl amine.

8. The device according to claim 1, wherein at least one component that is selected from nitroxyls, hydroxyl amines and hydroxyl amine salts is a hydroxyl amine salt.

9. The device according to claim 1 wherein X is phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate.

10. A The device according to claim 1 wherein at least one of the one or more nitroxyls, hydroxyl amines and hydroxyl amine salts of component (iii) is selected from the group consisting of
bis(1-oxyl-2,2-6-6-tetramethylpiperidin-4-yl) sebacate;
bis(1-hydroxy-2,2-6-6-tetramethylpiperidin-4-yl) sebacate;
1-hydroxy-2,2-6-6-tetramethyl-4-acetoxypiperidinium citrate;
1-oxyl-2,2,6,6-tetramethyl-4-acetamidopiperidine;
1-hydroxy-2,2,6,6-tetramethyl-4-acetamidopiperidine;
1-hydroxy-2,2,6,6-tetramethyl-4-acetamidopiperidinium bisulfate;
1-oxyl-2,2,6,6-tetramethyl-4-oxo-piperidine;
1-hydroxy-2,2,6,6-tetramethyl-4-oxo-piperidine;
1-hydroxy-2,2,6,6-tetramethyl-4-oxo-piperidinium acetate;
1-oxyl-2,2,6,6-tetramethyl-4-methoxy-piperidine;
1-hydroxy-2,2,6,6-tetramethyl-4-methoxy-piperidine;
1-hydroxyl-2,2,6,6-tetramethyl-4-methoxy-piperidinium acetate;
1-oxyl-2,2,6,6-tetramethyl-4-acetoxypiperidine;
1-hydroxy-2,2,6,6-tetramethyl-4-acetoxypiperidine;
1-oxyl-2,2,6,6-tetramethyl-4-propoxy-piperidine;
1-hydroxy-2,2,6,6-tetramethyl-4-propoxy-piperidinium acetate;
1-hydroxy-2,2,6,6-tetramethyl-4-propoxy-piperidine;
1-oxyl-2,2,6,6-tetramethyl-4-(2-hydroxy-4-oxapentoxy) piperidine;
1-hydroxy-2,2,6,6-tetramethyl-4-(2-hydroxy-4-oxapentoxy) piperidinium acetate;
1-oxyl-2,2,6,6-tetramethyl-4-hydroxypiperidine;
1-hydroxy-2,2,6,6-tetramethyl-4-hydroxypiperidine;
1-hydroxy-2,2,6,6-tetramethyl-4-hydroxypiperidinium chloride;
1-hydroxy-2,2,6,6-tetramethyl-4-hydroxypiperidinium acetate;
1-hydroxy-2,2,6,6-tetramethyl-4-hydroxypiperidinium bisulfate;
1-hydroxy-2,2,6,6-tetramethyl-4-hydroxypiperidinium citrate;
bis(1-hydroxy-2,2,6,6-tetramethyl-4-hydroxypiperidinium) citrate;
tris(1-hydroxy-2,2,6,6-tetramethyl-4-hydroxypiperidinium) citrate;
tetra(1-hydroxy-2,2,6,6-tetramethyl-4-hydroxypiperidinium) ethylenediaminetetraacetate;
tetra(1-hydroxy-2,2,6,6-tetramethyl-4-acetamidopiperidinium) ethylenediaminetetraacetate;
tetra(1-hydroxy-2,2,6,6-tetramethyl-4-oxopiperidinium) ethylenediaminetetraacetate;
penta(1-hydroxy-2,2,6,6-tetramethyl-4-hydroxypiperidinium) diethylenetriaminepentaacetate;
penta(1-hydroxy-2,2,6,6-tetramethyl-4-acetamidopiperidinium) diethylenetriaminepentaacetate;
penta(1-hydroxy-2,2,6,6-tetramethyl-4-oxopiperidinium) diethylenetriaminepentaacetate;
tri(1-hydroxy-2,2,6,6-tetramethyl-4-hydroxypiperidinium) nitrilotriacetate;
tri(1-hydroxy-2,2,6,6-tetramethyl-4-acetamidopiperidinium) nitrilotriacetate;
tri(1-hydroxy-2,2,6,6-tetramethyl-4-oxopiperidinium) nitrilotriacetate;
penta(1-hydroxy-2,2,6,6-tetramethyl-4-hydroxypiperidinium) diethylenetriaminepentamethylenephosphonate;
penta(1-hydroxy-2,2,6,6-tetramethyl-4-acetamidopiperidinium) diethylenetriaminepentamethylenephosphonate; and
penta(1-hydroxy-2,2,6,6-tetramethyl-4-oxopiperidinium) diethylenetriaminepentamethylenephosphonate.

11. The device according to claim 1 wherein at least one of the one or more nitroxyls, hydroxyl amines and hydroxyl amine salts of component (iii) is selected from the group consisting of
bis(1-oxyl-2,2-6-6-tetramethylpiperidin-4-yl) sebacate;
1-oxyl-2,2,6,6-tetramethyl-4-acetamidopiperidine;
1-oxyl-2,2,6,6-tetramethyl-4-oxo-piperidine;
1-oxyl-2,2,6,6-tetramethyl-4-methoxy-piperidine;
1-oxyl-2,2,6,6-tetramethyl-4-acetoxypiperidine;
1-oxyl-2,2,6,6-tetramethyl-4-propoxy-piperidine;
1-oxyl-2,2,6,6-tetramethyl-4-(2-hydroxy-4-oxapentoxy) piperidine;
1-oxyl-2,2,6,6-tetramethyl-4-hydroxypiperidine.

12. The electrochromic device according to claim 11, wherein the medium is an electrochromic medium which further comprises at least one anodic material; at least one cathodic material, wherein either or both of the anodic and cathodic materials are electroactive and at least one of the anodic and cathodic materials is electrochromic.

13. A The device according to claim 1 wherein at least one of the one or more nitroxyls, hydroxyl amines and hydroxyl amine salts of component (iii) is selected from the group consisting of
bis(1-hydroxy-2,2-6-6-tetramethylpiperidin-4-yl) sebacate;
1-hydroxy-2,2,6,6-tetramethyl-4-acetamidopiperidine;
1-hydroxy-2,2,6,6-tetramethyl-4-oxo-piperidine;
1-hydroxy-2,2,6,6-tetramethyl-4-methoxy-piperidine;
1-hydroxy-2,2,6,6-tetramethyl-4-acetoxypiperidine;
1-hydroxy-2,2,6,6-tetramethyl-4-propoxy-piperidine;
1-hydroxy-2,2,6,6-tetramethyl-4-hydroxypiperidine.

14. The device according to claim 1 wherein at least one of the one or more nitroxyls, hydroxyl amines and hydroxyl amine salts of component (iii) is selected from the group consisting of 1-hydroxy-2,2-6-6-tetramethyl-4-acetoxypiperidinium citrate;
bis(1-hydroxy-2,2,6,6-tetramethyl-4-acetoxypiperidinium) citrate;
tris(1-hydroxy-2,2,6,6-tetramethyl-4-acetoxypiperidinium) citrate;
1-hydroxy-2,2,6,6-tetramethyl-4-acetamidopiperidinium bisulfate;
1-hydroxy-2,2,6,6-tetramethyl-4-oxo-piperidinium acetate;
1-hydroxy-2,2,6,6-tetramethyl-4-oxo-piperidinium citrate;
bis(1-hydroxy-2,2,6,6-tetramethyl-4-oxo-piperidinium) citrate;
tris(1-hydroxy-2,2,6,6-tetramethyl-4-oxo-piperidinium) citrate;
1-hydroxyl-2,2,6,6-tetramethyl-4-methoxy-piperidinium acetate;
1-hydroxy-2,2,6,6-tetramethyl-4-propoxy-piperidinium acetate;
1-hydroxy-2,2,6,6-tetramethyl-4-(2-hydroxy-4-oxapentoxy)piperidinium acetate;
1-hydroxy-2,2,6,6-tetramethyl-4-hydroxypiperidinium chloride;
1-hydroxy-2,2,6,6-tetramethyl-4-hydroxypiperidinium acetate;
1-hydroxy-2,2,6,6-tetramethyl-4-hydroxypiperidinium bisulfate;
1-hydroxy-2,2,6,6-tetramethyl-4-hydroxypiperidinium citrate;
bis(1-hydroxy-2,2,6,6-tetramethyl-4-hydroxypiperidinium) citrate;
tris(1-hydroxy-2,2,6,6-tetramethyl-4-hydroxypiperidinium) citrate;
1-hydroxy-2,2,6,6-tetramethyl-4-acetamidopiperidinium citrate;
bis(1-hydroxy-2,2,6,6-tetramethyl-4-acetamidopiperidinium) citrate;
tris(1-hydroxy-2,2,6,6-tetramethyl-4-acetamidopiperidinium) citrate;
tetra(1-hydroxy-2,2,6,6-tetramethyl-4-hydroxypiperidinium) ethylenediaminetetraacetate;
tetra(1-hydroxy-2,2,6,6-tetramethyl-4-acetamidopiperidinium) ethylenediaminetetraacetate;
tetra(1-hydroxy-2,2,6,6-tetramethyl-4-oxopiperidinium) ethylenediaminetetraacetate;
penta(1-hydroxy-2,2,6,6-tetramethyl-4-hydroxypiperidinium) diethylenetriaminepentaacetate;
penta(1-hydroxy-2,2,6,6-tetramethyl-4-acetamidopiperidinium) diethylenetriaminepentaacetate;
penta(1-hydroxy-2,2,6,6-tetramethyl-4-oxopiperidinium) diethylenetriaminepentaacetate;
tri(1-hydroxy-2,2,6,6-tetramethyl-4-hydroxypiperidinium) nitrilotriacetate;
tri(1-hydroxy-2,2,6,6-tetramethyl-4-acetamidopiperidinium) nitrilotriacetate;
tri(1-hydroxy-2,2,6,6-tetramethyl-4-oxopiperidinium) nitrilotriacetate;
penta(1-hydroxy-2,2,6,6-tetramethyl-4-hydroxypiperidinium) diethylenetriaminepentamethylenephosphonate;
penta(1-hydroxy-2,2,6,6-tetramethyl-4-acetamidopiperidinium) diethylenetriaminepentamethylenephosphonate; and
penta(1-hydroxy-2,2,6,6-tetramethyl-4-oxopiperidinium) diethylenetriaminepentamethylenephosphonate.

15. The device according to claim 1, wherein at least one of the one or more nitroxyls, hydroxyl amines and hydroxyl amine salts of component (iii) is a hydroxyl amine or hydroxyl amine salt of formula IV or V $$R_1R_2N\text{—}OH \tag{IV}$$

$$(R_1R_2N\text{—}OH)\cdot(HY) \tag{V}$$

where
  $R_1$ is alkyl of 1 to 36 carbon atoms, cycloalkyl of 5 to 12 carbon atoms or aralkyl of 7 to 9 carbon atoms; or $R_1$ is said alkyl, cycloalkyl or aralkyl substituted by one to six alkyl of 1 to 12 carbon atoms, halogen, cyano, $E_1O\text{—}$, $E_1CO\text{—}$, $E_1OCO\text{—}$, $E_1COO\text{—}$, $E_1S\text{—}$, $E_1SO\text{—}$, $E_1SO_2\text{—}$, $\text{—}NH_2$, $\text{—}NHE_1$, $\text{—}NE_1E_2$, $\text{—}PO(OE_1)(OE_2)$ or $\text{—}OPO(OE_1)(OE_2)$ groups;
  $R_2$ is hydrogen or independently has the same meaning as $R_1$, where at least one of $R_1$ and $R_2$ contains a hydrogen alpha to the —NOH moiety; or
  $R_1$ and $R_2$ together form a $C_{2-12}$heterocyclic ring which contains at least one carbon substituted hydrogen alpha to the —NOH moiety, where said $C_{2-12}$heterocyclic ring is unsubstituted or is substituted by one to three alkyl of 1 to 12 carbon atoms, halogen, cyano, $E_1O\text{—}$, $E_1CO\text{—}$, $E_1OCO\text{—}$, $E_1COO\text{—}$, $E_1S\text{—}$, $E_1SO\text{—}$, $E_1SO_2\text{—}$, $\text{—}NH_2$, $\text{—}NHE_1$, $\text{—}NE_1E_2$, $\text{—}PO(OE_1)(OE_2)$ or $\text{—}OPO(OE_1)(OE_2)$ groups; or where said $C_{2-12}$heterocyclic ring is interrupted by one to three $\text{—}O\text{—}$, $\text{—}NE_1\text{—}$, $\text{—}CO\text{—}$, $\text{—}CONE_1\text{-}$, $\text{—}S\text{—}$, $\text{—}SO\text{—}$, $\text{—}SO_2\text{—}$, $\text{—}COO\text{—}$, $\text{—}PO_3\text{—}$ or $\text{—}PO_4E_1$ groups; or where said heterocyclic ring is both substituted and interrupted by said groups;
  $E_1$ and $E_2$ independently are hydrogen, alkyl of 1 to 4 carbon atoms or alkyl of 1 to 4 carbon atoms substituted by one to three hydroxyl groups; or $E_1$ and $E_2$ independently are an oligomer of poly(ethylene glycol) or poly(propylene glycol) terminated by hydroxyl, methoxy, acetate or propionate, where the oligomer has a molecular weight up to about 500, and
  X is an inorganic or organic anion, and
where the total charge of cations h is equal to the total charge of anions j.

16. The device according to claim 15 wherein X is phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate.

17. The device according to claim 1 wherein the ultraviolet light absorbers and the additive selected from nitroxyls, hydroxyl amines and hydroxyl amine salts, in total, are present from about 0.05% to about 30% by weight, based on the weight of the solvent.

18. The device according to claim 1 wherein at least one of the one or more solvents is selected from the group consisting of esters, epoxides, vinyl ethers, aromatic hydrocarbons, halogenated organic solvents, saturated linear or branched hydrocarbons, silicone oils, and low molecular weight halogen-containing polymers.

19. An electroactive device according to claim 1, wherein the electroactive device is an electrochromic device.

20. A method of preparing a stabilized medium useful in electroactive devices, which method comprises adding an effective amount of one or more additive compounds selected from the group consisting of nitroxyls, hydroxyl amines and hydroxyl amine salts wherein at least one of the one or more nitroxyls, hydroxyl amines and hydroxyl amine salts is a compound of formula I, II or III

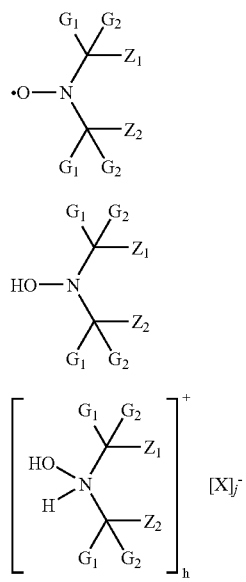

where

G$_1$ and G$_2$ are independently alkyl of 1 to 4 carbon atoms or are together pentamethylene, Z$_1$ and Z$_2$ are each methyl, or Z$_1$ and Z$_2$ together form a linking moiety which may additionally be substituted by an ester, ether, hydroxy, oxo, cyanohydrin, amide, amino, carboxy or urethane group, X is an inorganic or organic anion, and where the total charge of cations h is equal to the total charge of anions j, to a composition comprising:

i) one or more solvents suitable as a medium in an electroactive device, and ii) an effective amount of one or more additive compounds selected from the group consisting of ultraviolet light absorbers, wherein the electroactive device further contains a pair of electrodes and at least one compound or material that changes transmittance upon or after application of an electric stimulus.

* * * * *